United States Patent [19]

Haseltine et al.

[11] Patent Number: 5,604,114
[45] Date of Patent: Feb. 18, 1997

[54] CIS-ACTING REPRESSION SEQUENCES, CIS-ACTING ANTIREPRESSION SEQUENCES, VECTORS, METHODS OF PREPARATION AND USE

[75] Inventors: William A. Haseltine, Cambridge, Mass.; Craig A. Rosen, Glen Ridge, N.J.; Joseph G. Sodroski, Cambridge; Ernest Terwilliger, Boston, both of Mass.; Wei C. Goh, Stanford, Calif.

[73] Assignee: Dana-Farber Cancer Institute, Boston, Mass.

[21] Appl. No.: 41,887

[22] Filed: Apr. 2, 1993

Related U.S. Application Data

[63] Continuation of Ser. No. 847,854, Mar. 9, 1992, abandoned, which is a continuation of Ser. No. 591,667, Sep. 27, 1990, abandoned, which is a continuation of Ser. No. 56,620, May 29, 1987, abandoned, which is a continuation-in-part of Ser. No. 865,151, May 20, 1986, Pat. No. 4,935,372.

[51] Int. Cl.⁶ .......................... C12N 15/11; C12N 15/49; C12N 15/63; C12N 15/85
[52] U.S. Cl. ................. 435/69.1; 435/172.3; 435/320.1; 536/23.1
[58] Field of Search ............................ 435/320.1, 172.3, 435/69.1; 536/23.1

[56] References Cited

U.S. PATENT DOCUMENTS 4,935,372  6/1990  Haseltine et al. ................. 435/69.3 X

FOREIGN PATENT DOCUMENTS 0187041   7/1986   European Pat. Off. .
0233764   8/1987   European Pat. Off. .
WO-A-
8505636   12/1985  WIPO .

OTHER PUBLICATIONS

Sodroski, et al., Nature 321:412–417 (1986).
Rosen, et al., Cell 41:813–823 (1985).
M.H. Malim et al (1989) Proc. Natl. Acad. Sci. USA 86:8222–8226.
M. Guyader et al (1987) Nature 326:662–669.
V. Hirsch et al (1987) Cell 49:307–319.
P. J. Dillon et al (1990) J. Virol. 64(9):4428–4437.
B. R. Cullen et al (1988) J. Virol. 62:2498–2501.

*Primary Examiner*—George C. Elliott
*Assistant Examiner*—Johnny F. Railey, II
*Attorney, Agent, or Firm*—David G. Conlin; Ronald I. Eisenstein

[57] ABSTRACT

Cis-acting repression sequences which are able to provide a cis-acting inhibitory effect on the expression of a gene when placed downstream of the gene in its untranslated message are dislcosed. Cis-acting anti-repression sequences which can relieve the cis-acting repression in the presence of the art gene product are also disclosed. These sequences correspond to a sufficient number of nucleotides from the HIV-I, HIV-2, STLV-3 or HTLV-IV genomes to provide the repression or anti-repression effects. The use of the sequences in vectors and systems to control the expression of a desired gene product is also described.

27 Claims, 11 Drawing Sheets

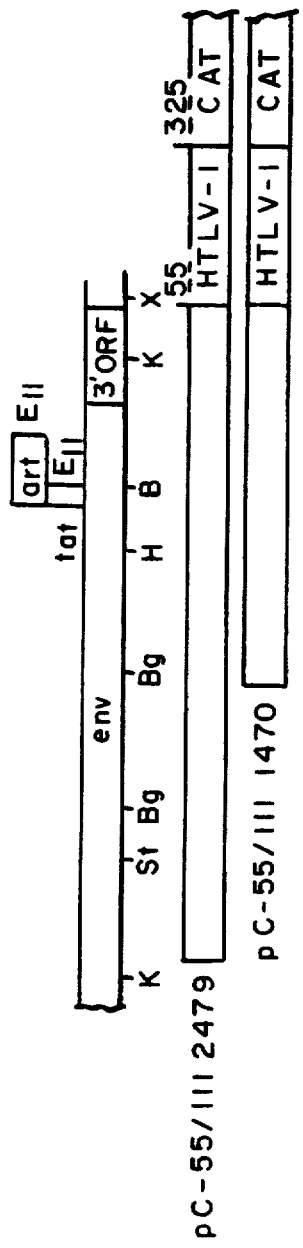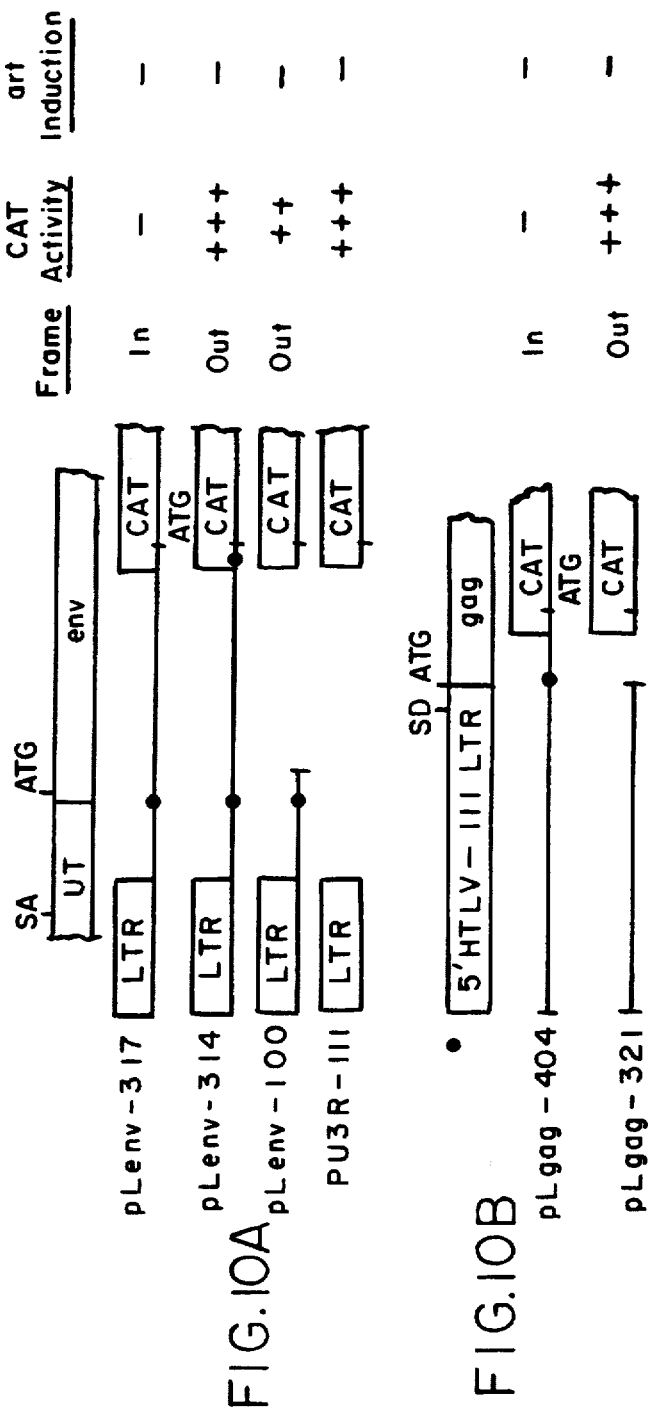

CIS-ACTING REPRESSION SEQUENCES, CIS-ACTING ANTIREPRESSION SEQUENCES, VECTORS, METHODS OF PREPARATION AND USE

This is a continuation of application Ser. No. 07/847,854, filed on Mar. 9, 1992, now abandoned, which is a continuation of Ser. No. 07/591,667, fled Sep. 27, 1990, now abandoned, which is a continuation of Ser. No. 07/056,620, filed May 29, 1987, now abandoned, which is a continuation in part of Ser. No. 06/865,151, filed May 20, 1986, now U.S. Pat. No. 4,935,372.

The present invention is directed to the use of vectors, transformants and cell lines containing cis-acting repression DNA sequence(s), cis-acting anti-repression DNA sequences and the use of such DNA sequence(s) to control the synthesis of proteins. Most preferably, the cis-acting repression sequence is used in conjunction with the cis-acting anti-repression sequence and art gene product to regulate and control the expression of heterologous gene products.

The human immunodeficiency virus (HIV-I, also referred to as HTLV-III, LAV or HTLV-III/LAV) is the etiological agent of the acquired immune deficiency syndrome (AIDS) and related disorders [Barre-Sinoussi, et al., *Science* 220, 868–871 (1983); Gallo et al., *Science* 224, 500–503 (1984); Lane et al., 1984; Levy et al., *Science* 225:840–842 (1984); Popovic et al., *Science* 224, 497–500 (1984); Sarngadharan et al., *Science* 224:506–508 (1984); Siegal et al., *N. Engl, J. Med.* 305:1439–1444 (1981)]. The disease is characterized by a long asymptomatic period followed by progressive degeneration of the immune system and the central nervous system. Studies of the virus indicate that replication is highly regulated, and both latent and lytic infections of the CD4 positive helper subset of T lymphocytes occur in tissue culture [Zagury et al., *Science* 231:850–853 (1986)]. The expression of the virus in infected patients also appears to be regulated, as the titer of infectious virus remains low throughout the course of the disease. Molecular studies of the replication and genomic organization of HIV-I show that it encodes at least seven genes [Ratner et al., *Nature* 313:277–284 (1985); Sanchez-Pescador et al., *Science* 227:484–492 (1985); Muesing et al., *Nature* 313:450–457 (1985); Wain-Hobson et al., (1985)]. Three of the genes, the gag, pol, and env genes, are common to all retroviruses. However, the genome also encodes four additional genes that are not common to most retroviruses, the sor, tat, art, (now referred to as rex), and 3' orf (now referred to as nef), genes [Sodroski et al., *Science* 231:1549–1553 (1986); Arya et al., *Science* 229:69–73 (1985); Sodroski et al., *Science* 227:171–173 (1985); Sodroski et al., *Nature* 321:412–417 (1986); Feinberg et al., *Cell* 46:807–817 (1986)].

Mutations in two of these genes, the sor gene, which encodes a 23 kd protein [Sodroski, J. et al., *Science* 231:1549–1553 (1986), Lee, T. H. et al., *Science* 231:1546–1549 (1986)] and the 3'orf gene, which encodes a 27 kd protein [Allan, J. S., et al., *Science* 230:810–812 (1985)] do not eliminate the ability of the virus to replicate in and to kill T-lymphocytes [Sodroski, J. et al., *Science*, 231, supra].

The trans-activator ($tat_{III}$) gene encodes a 14 kd protein that post-transcriptionally stimulates HIV-I long-terminal repeat-(LTR) directed gene expression [U.S. patent application Ser. No. 806,263, filed Dec. 6, 1985; Rosen, C. A., et al., *Nature* 319:555–559 (1986); Sodroski, J. G., et al., *Science* 227:171–173 (1985); Arya, S., et al., *Science* 229, supra and Sodroski, J. et al., *Science* 229: supra, which are all incorporated herein by reference] via an interaction with specific target sequences called TAR in the leader of viral messages [Rosen, C. A., et al., *Cell* 41:813–823 (1985)]. Mutations in the 5'portion of the first coding exon of the bipartate $tat_{III}$ gene destroy the ability of the virus to efficiently synthesize structural proteins and to replicate [U.S. patent application Ser. No. 806,263; Dayton, A. et al., *Cell* 44:941–497 (1986)] These mutations can be complemented in trans in cell lines that constitutively express the $tat_{III}$ protein.

We have also discovered that the art gene is necessary for the expression of the capsid and the envelope protein [U.S. patent application Ser. No. 865,151, filed May 20, 1986; Sodroski et al, *Nature* 321:412–417 (1986), both of which are incorporated herein by reference]. Our observation that functional tat gene product can be made by art-defective proviruses indicates that the art gene acts as a post-transcriptional regulator.

It would be extremely useful to have a system for regulating the expression of a desired protein. While it is possible to use the $tat_{III}$ gene product to produce high level of heterologous gene products, the production of certain gene products, such as the env protein, can result in lysis of the cell. Consequently, the cell will die before having produced large amounts of the desired protein.

Further, some cells possess proteolytic enzymes that break down heterologous protein and prevent the accumulation of large amounts of the heterologous protein.

We discovered a method where the art gene product negates the effect of a cis-acting negative regulatory sequence thus allowing the control of the expression of desired proteins.

It would be very desirable to know and be able to produce specific sequences which result in cis-acting inhibitory properties. Especially, where these inhibitory sequences are responsive to repression by another protein, such as the art gene product. Knowing discrete sequences which will provide these properties permits the use of smaller portions of nucleotides corresponding to the viral genome in regulatory system.

Still further, by knowing how the HIV-I virus replicates, it is possible to open new modes of attack on the virus's ability to efficiently synthesize structural protein and to replicate.

SUMMARY OF INVENTION

We have now discovered certain DNA sequences that will supress the expression of heterologous genes and a method for regulating expression of a desired protein.

The DNA sequences that can suppress the expression of heterologous gene products are referred to herein as cis-acting repression (CRS) sequences. Those sequences that in the presence of the art protein will counteract (or repress) the suppression of the CRS sequences are referred to as cis-acting anti-repression (CAR) sequences (now referred to as Rev Responsive Element (RRE)). Many of these DNA sequences form part of a larger DNA segment that is referred to as the art regulatory region envelope (ARE).

In certain embodiments, these sequences can be derived from nucleotide sequences substantially corresponding to the nucleotide sequences in the HIV-I genome. Specifically, the ARE region corresponds to a sufficient number of nucleotides from 6376–7760 to provide both cis-acting repression regulatory properties and be responsive to the anti-cis-acting regulatory property of the art gene product. The use of a sequence corresponding to the ARE region is preferred.

$CRS_1$ corresponds to a sufficient number of nucleotides from 6376–6725 of the HIV-I genome to provide cis-acting repression properties. $CRS_2$ corresponds to a sufficient number of nucleotides from 7283–7325 to provide cis-acting repression properties. $CRS_3$ corresponds to a sufficient number of nucleotides from the region 5893–6538 to provide cis-acting repression properties. $CRS_4$ corresponds to a sufficient number of nucleotides from the region 8204–8597 to provide cis-acting repression properties.

$CRS_4$ corresponds to a region of the HIV-I genome that is outside of the env gene and within the 3'orf gene sequence. Although, it strongly effects the expression of heterologous gene products, it has not been demonstrated to have a similar effect on HIV-I viral proteins. For the greatest inhibitory effect on protein expression, the $CRS_1$ and $CRS_4$ sequences are preferred. They can suppress the expression of heterologous gene products up to about 100 times when compared to wild-type cells. This inhibition can be offset by the presence of the art gene product.

These regulatory sequences are in a vector downstream in the untranslated message of a gene whose expression is to be controlled.

These sequences can be used in controlling the production of a desired gene product. This method includes:
(a) transfecting a preselected cell line with a vector containing a desired heterologous gene fused upstream of a cis-acting repression sequence and a cis-acting anti-repression sequence responsive to art gene product; and
(b) at a predetermined time contacting the cis-acting anti-repression sequence with a sufficient amount of art gene product to activate the cis-acting anti-repression system to repress the cis-acting repression sequence and permit expression of the desired heterologous gene product.

BRIEF DESCRIPTION OF THE FIGURES

FIG. 9 is an illustration of enhancer test plasmids.

FIG. 10A and FIG. 10B are schematic representations showing activity of hybrid plasmids that contain the gag and env gene leader region sequences.

DETAILED DESCRIPTION OF THE INVENTION

The non-structural genes are synthesized from messenger RNA (mRNA) species that are different from those used for the structural genes (i.e. gag and env) [Muesing et al., *Nature* 313:450–457 (1985); Arya et al., supra). The tat and art genes are synthesized from mRNAs from which most of the information encoding the virion structural proteins is removed by splicing (FIG. 1).

Figure 1:
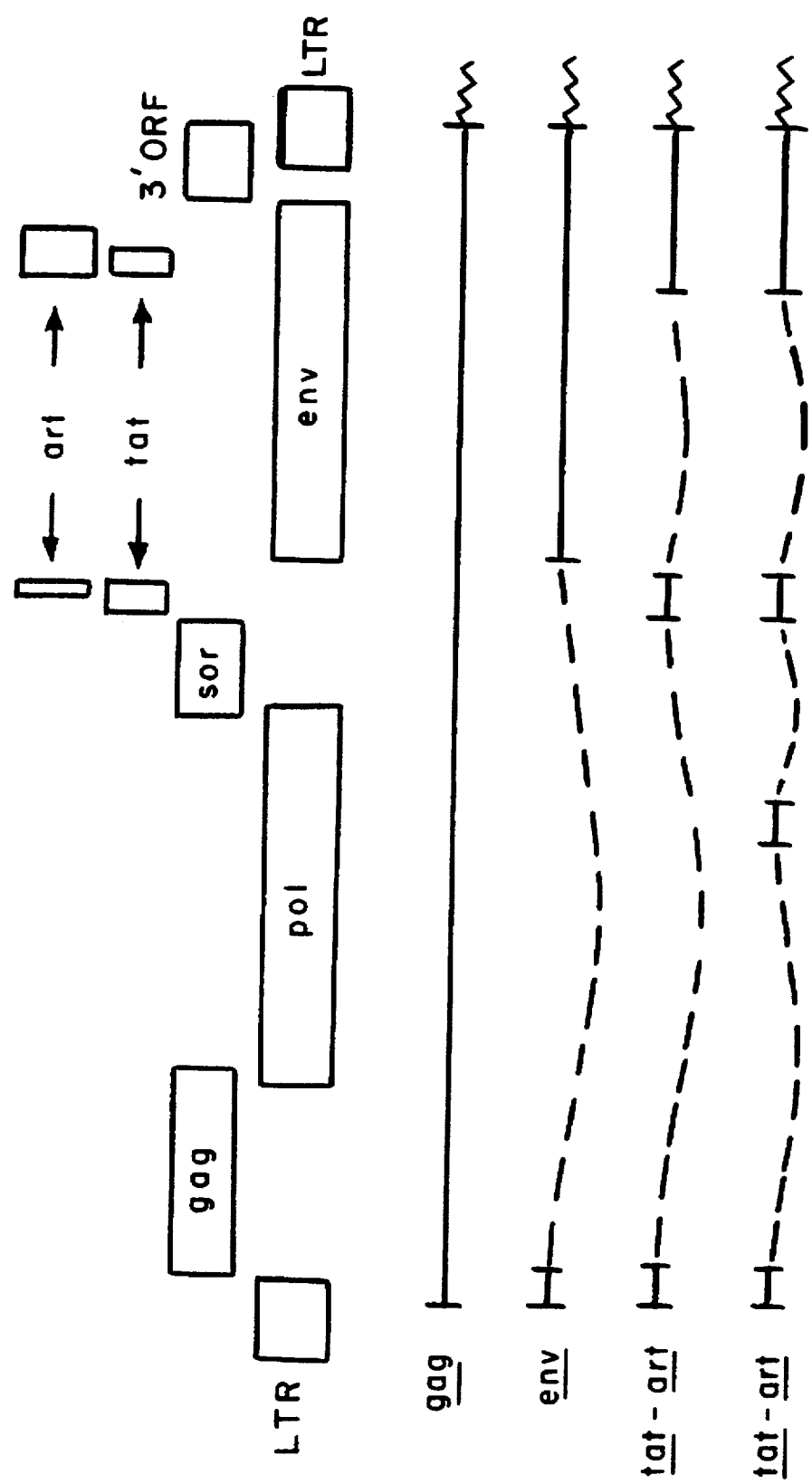
FIG. 1 is a schematic illustration of the splicing events used to produce the HIV-I mRNAs shown.

FIG. 1 illustrates the splicing events used to produce the HIV-I mRNAs shown. The exons present within the gag, env, tat and art mRNAs are depicted by solid lines. These exons were determined by analysis of HIV-I cDNA clones. The broken lines represent intron sequences spliced from the final transcript.

Art gene mutants show a defect in replication which appears to occur at a late stage of infection as some viral RNA can be made upon transfection of susceptible cells with proviruses defective for this gene. Neither the capsid nor the envelope gene proteins can be detected in cells transfected with the mutant proviruses [Sodroski et al., *Nature* 321, supra; Feinberg, supra]. Significantly, a functional tat gene product is made by art defective proviruses [Sodroski et al., *Nature* 321, supra]. This indicates that the art gene acts as a post-transcriptional regulator of the virion structural genes as all of the viral proteins are synthesized from mRNAs derived from splicing of the same primary transcript (FIG. 1). [See also Knight et al., *Science* 236:837–840 (1987)].

We have now discovered specific DNA sequences that can be used to suppress the expression of heterologous genes. These repression sequences should be placed downstream of the gene whose gene product is to be regulated because unlike the $tat_{III}$ gene product, these are cis-acting sequences. Those sequences that have an inhibitory effect on the expression are referred to as cis-acting repression (or regulatory) sequences (CRS). These sequences generally correspond to sequences in the 3' portion of the HIV-I, HIV-2, human T-lymphotropic virus (HTLV) type 4 and simian T-lymphotropic virus (STLV) type 3 genomes. There are also discrete sequences that are responsive to the respective art gene product and in the presence of a sufficient amount of such art gene product counteract the repression by the CRS and are referred to herein as cis-acting anti-repression (CAR) sequences (now referred to as Rev Responsive Element (RRE)). Vectors containing CSR sequences, CAR sequences and a desired gene can be constructed based upon the present disclosure by using techniques well known in the field. These vectors do not contain the entire viral genome. In one preferred embodiment they do not contain the art gene.

Preferably, the desired gene under cis-acting regulation is a heterologous gene.

Preferably, the CRS and CAR sequences correspond to nucleotide sequences from the HIV-I genome. However, nucleotide sequences corresponding to other viral genomes can also be used. HIV-2 also contains tar and art regulatory sequences and show trans-activation [Guyader, M., et al., *Nature* 326:662–669 (1987)], in addition to its structural genes. The CRS and CAR regions based upon this virus preferably correspond to a sufficient number of nucleotides from the env region for the CRS(s) to provide a cis-acting inhibitory (regulatory) effect on an upstream gene when it is in the untranslated message of the gene and for the CAR region(s) to counteract this inhibitory effect in the presence of art gene product. STLV-3 and HTLV-IV also have tat and art regulatory sequences which appear to be structurally and functionally similar to HIV-I, as well as structural genes [Hirsch, V., et al., *Cell* 49:307–319 (1987)]. CRS and CAR sequences based upon these viruses preferably correspond to a sufficient number of nucleotides from the env region for the CRS to provide a cis-acting repression effect on an upstream gene when it is in the untranslated message of that gene and for the CAR region to counteract the inhibitory effect of the CRS in the presence of art gene product. The CAR sequence is preferably contacted with an art protein or corresponding to the art gene product produced by the particular virus the CAR sequence is derived from.

The vector is used to transfect a cell by techniques well known in the art. Preferably, the vector also contains the corresponding viral LTR. The transfected cell will accumulate mRNA for the expression of the desired gene product, but will not express the gene product until the art gene product is added. In a preferred embodiment the use of the corresponding viral LTR and tat protein will result in enhanced expression of the desired gene product.

The art gene product can be added by a variety of techniques well known to the skilled artisan. For example, the cell can be co-transfected with a vector expressing the art gene product at a predetermined time. The art gene product (produced synthetically or by culturing and purification) can be added directly to the cell at the desired time. Alternatively, the initial vector could contain the art gene but have the art gene under the control of a secondary factor.

In a preferred method the art gene is already present in an art cell line and is under the control of the above-described secondary factor.

This application uses the HIV-I genome as exemplary, although it should be understood that the statements are generally applicable to the other viral genomes discussed.

The following DNA sequences can be used and contain nucleotides corresponding to a sufficient number of the nucleotides as set forth from the HIV-I genome to provide a cis-acting repression effect on a desired gene when inserted downstream of the gene in the gene's untranslated message.
(a) $CRS_1$ corresponds to a sufficient number of nucleotides from region 6376–6725;
(b) $CRS_2$ corresponds to a sufficient number of nucleotides from region 7283–7325.
(c) $CRS_3$ corresponds to a sufficient number of nucleotides from region 5893–6538; and
(d) $CRS_4$ corresponds to a sufficient number of nucleotides from region 8204–8597.
$CRS_1$ or $CRS_4$ are preferred for the greatest inhibitory effect on protein expression. In order to be able to express the gene one must use a CAR sequence as well as a CSR sequence.

Figure 2A:
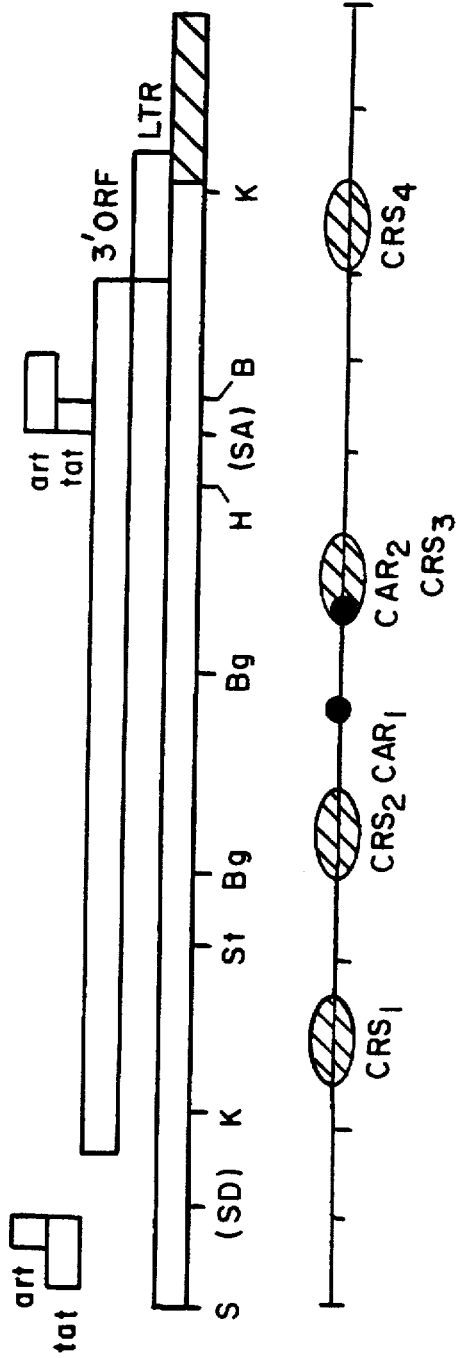
FIG. 2A is a line drawing showing the location of cis-acting repression sequences identified within the intragenic HIV-I sequences.

FIG. 2A shows the corresponding location of the above HIV-I CSR's and CAR's in the intragenic HIV-I sequences.

By use of HIV-I deletion mutants we have been able to demonstrate that the above regulatory sequences function as indicated. The CRS's negatively regulate the expression of heterologous genes, such as chloramphenicol acetyltransferase (CAT) and human growth hormone (hGH), and their effect is counteracted by the CAR sequences in the presence of the art gene product.

Many of these CSR and CAR sequences are located entirely within an intron in the env sequence of the HIV-I genome, region 6376–7760. The intron containing these sequences is referred to as the art regulatory region env (ARE). The regulatory effects of the env gene sequences on heterologous gene expression such as CAT do not depend on the HIV-I LTR sequences as the 5' LTR can be replaced with heterologous gene promoter elements and the 3'LTR can be replaced with a heterologous polyadenylation signal without effecting the control.

At least four regions within the 3' half of the HIV-I provirus which decrease the level of heterologous gene expression were detected. Removal of sequences located between nucleotides 6376 and 6725 as defined by the plasmid pairs pIIIAR/pAR-2 and pA-6376/pA-6725 results in an increase of CAT gene expression by a factor of ten or more and thus define a negative cis-acting regulatory sequence (CRS1). A second strong inhibitory effect on heterologous gene expression was observed for sequences located between nucleotides 8204 and 8597 (CRS4) as exemplified by the plasmid pair pIIIAR/pAR-7. Other less potent inhibitory sequences are located between nucleotides 7283 and 7325 (CRS2) and nucleotides 5893 and 6538 (CRS3) as defined by the plasmid pairs pA-7283/pA-7325 and pAR-2SV/pAR-3SV, respectively. One of these repression elements (CRS4) is located outside of the envelope gene, within the 3'orf gene near the 3' LTR. The effect of the CRS's, $CRS_4$ in particular, can be dependent upon the sequence context as both functional tat and art genes can be produced from cDNA clones that contain $CRS_4$ but which lack the CAR sequences.

More preferably, a segment containing a sufficient number of nucleotides corresponding to the ARE region (i.e. 6376–7760 of the HIV-I genome) to provide a cis-acting repression effect on a desired gene in the absence of art gene product wherein this cis-acting regulatory effect is counteracted in the presence of the art gene product is used. This segment is placed downstream in the untranslated message of the gene whose expression is to be controlled. This segment corresponds to sequences entirely between the major splice donor and acceptor sequences within the env gene. It is expected that ARE regions are located in corresponding portions of the HIV-2, STLV-3 and HTLV-IV genome.

Figure 11:
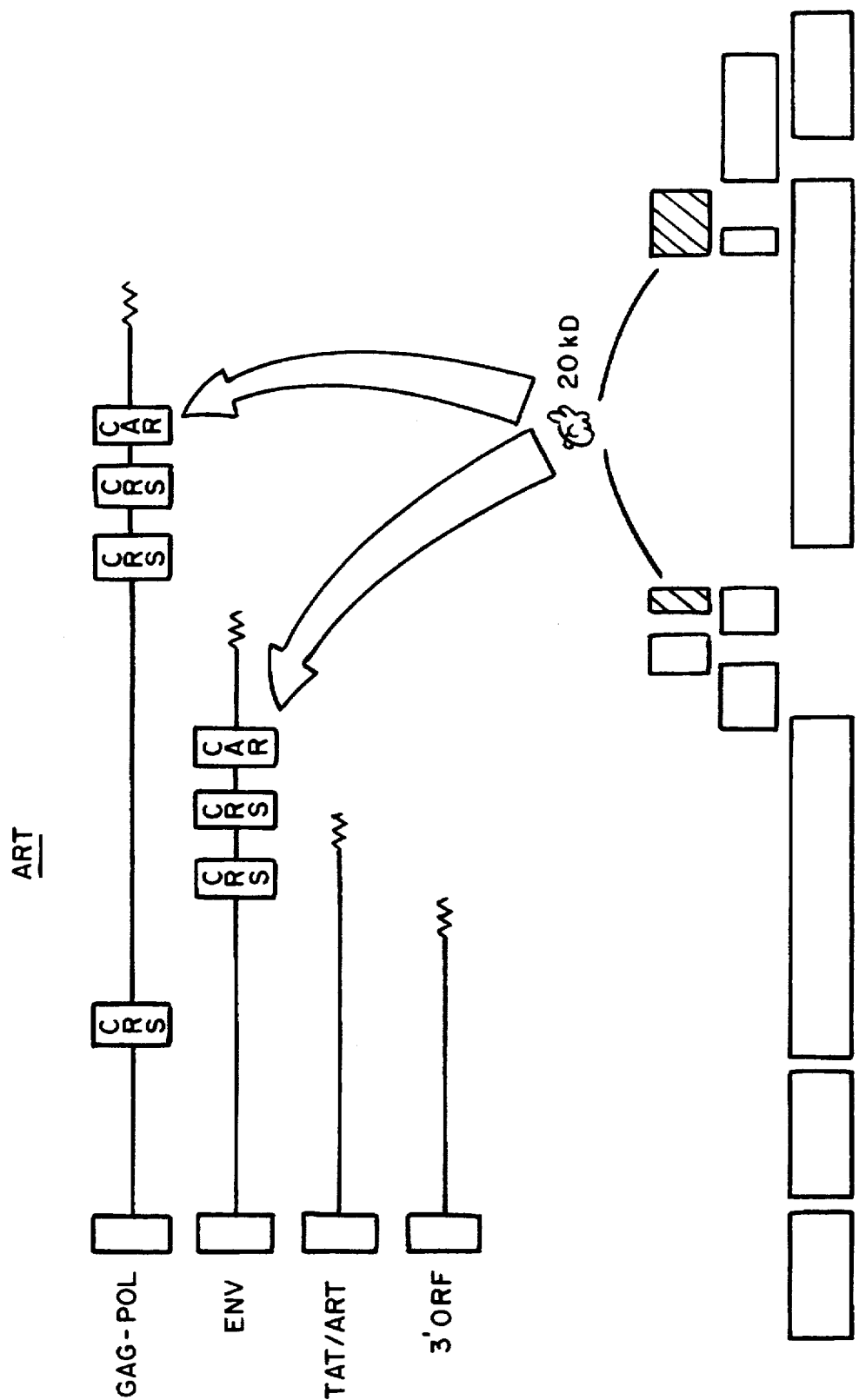
FIG. 11 shows the interaction between the 20 kD art gene product and the CAR region of a gene under the control of CRS and CAR sequences.
Figure 12:
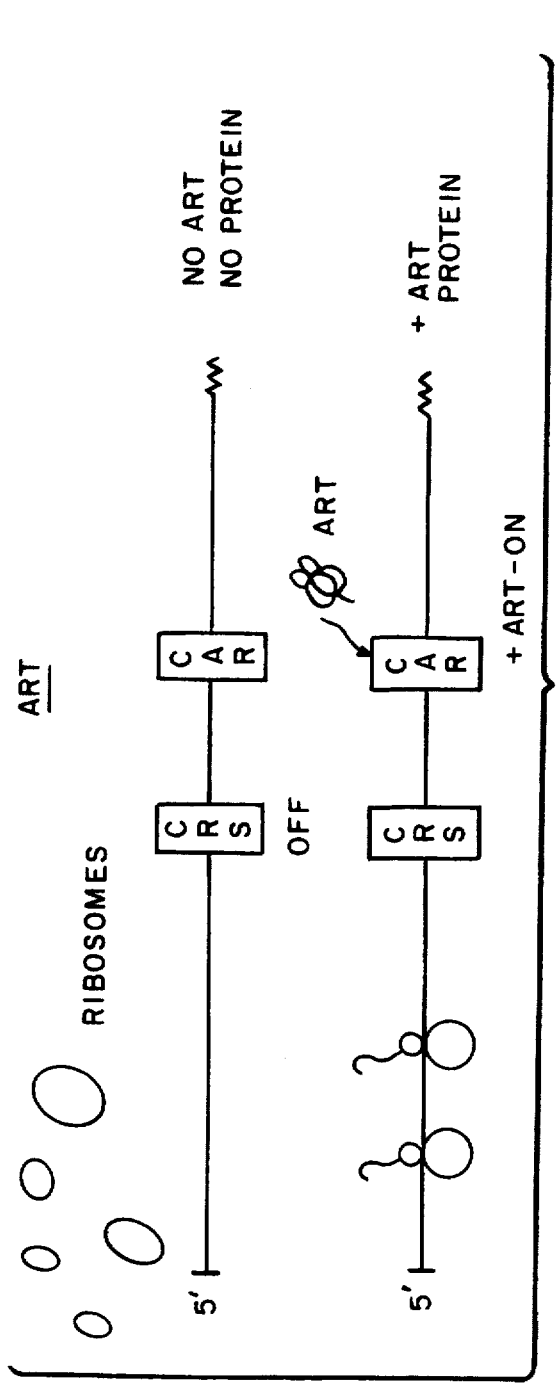
FIG. 12 illustrates a postulated mechanism for the art/cis regulatory control.

The present invention permits the development of a multi-tiered gene expression system. For example, by placing a desired gene, preferably a heterologous gene, under the control of a CRS one can prevent the expression of the desired gene until the CRS's inhibitory effect is counteracted by a CAR sequence that has been "turned on" by exposure to a sufficient amount of the art gene product. Although not wishing to be bound by theory it is believed the CRSs turn off the translation of any mRNA that contains them. The CAR sequences, in the presence of the art protein, turn back on the translation of messages that contain the CRS. See FIGS. 11 and 12. FIG. 11 shows the postulated interaction between the 20 kD art protein and the CAR region of the genefs mRNA. FIG. 12 shows the translation of mRNA containing a CRS and CAR "turned off" in the absence of art protein and "turned on" in the presence of art.

Figure 13:
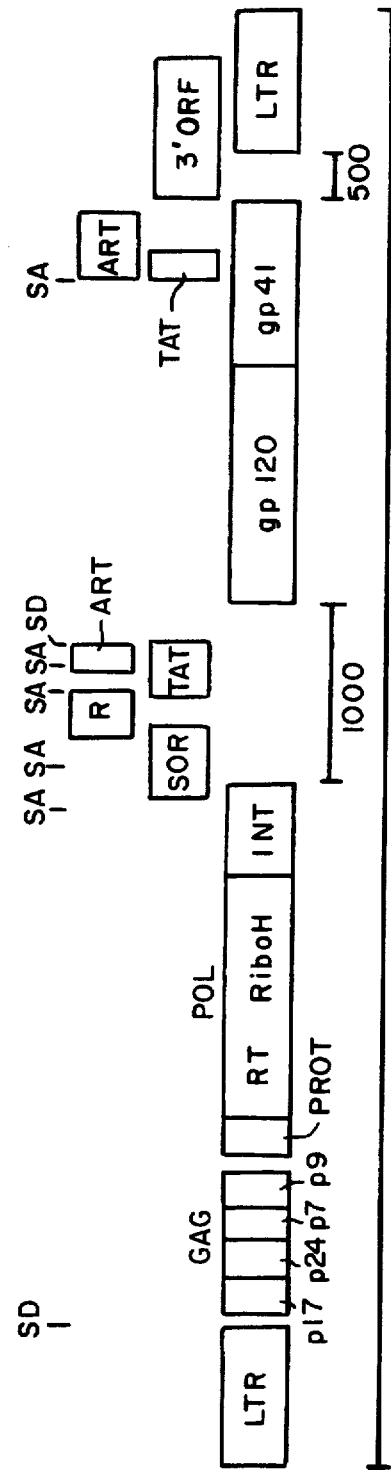
FIG. 13 is a schematic illustration of the HIV-I genome.
Figure 14:
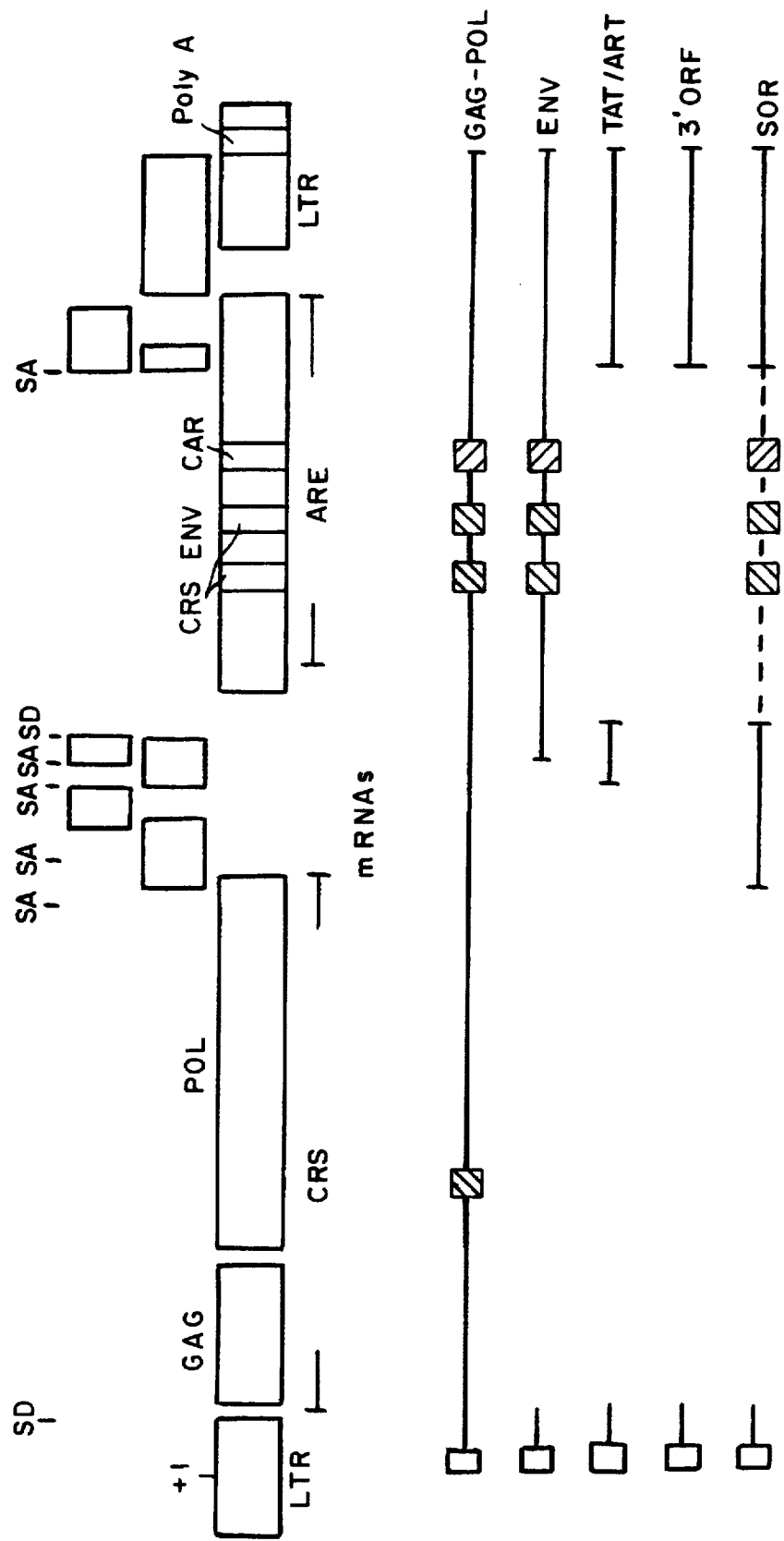
FIG. 14 shows CRS, CAR and ARE regions in the HIV-I genome and mRNA.

In addition to the CRSs in the env gene there is at least one CRS in the gag-pol gene. FIG. 13 is a schematic illustration of the HIV-I genome. FIG. 14 shows CRS sequences in the ARE region, and in the GAG-POL region. Messenger RNAs for the regulatory and structural genes are also shown. Gag, pol and env contain CRS and CAR sequences, which prevent their expression except in the presence of art and CAR, while tat, art and 3'orf do not contain such sequences and are expressed independently of art. In order for the CRS inhibitory effect to be relieved by the art gene product a CAR region must be present within the same gene.

Preferably, the gene product is under the control of the HIV-I LTR sequences. Thereafter, when expression is ultimately carried out, if the $tat_{III}$ gene product is present very high levels of protein production will occur. However, these LTRsvs can be replaced, for example, the 5' LTR can be replaced with heterologous promoter elements and the 3' LTR can be replaced with a heterologous polyadenylation signal. In one preferred embodiment of such a system an HTLV-I or II LTR is used. Such LTR's can also be activated in trans by $tat_I$ or $tat_{II}$ gene products to result in increased expression of the desired gene product.

One could use an expression vector of the type described herein containing, for example, an HIV-I LTR sequence, downstream of the sequence is the desired gene minus its polyadenylation sequences and fused to the gene in its untranslated message are CRS and CAR sequences. This vector would not contain a functional art gene unless the art gene was under the control of a secondary factor. Preferably, the vector would not contain the art gene. In a preferred embodiment the vector would contain sufficient nucleotides corresponding to the ARE sequence. Preferably, sufficient nucleotides of the $tat_{III}$ gene to express functional $tat_{III}$ gene product are also present. Such a vector can readily be constructed by one of ordinary skill in the art.

Thereafter, the vector would be used to transfect a cell. If the vector used does not contain the $tat_{III}$ sequence, then the cell would preferably also be contacted with $tat_{III}$ gene product. Such contacting can be accomplished by a variety of methods. For example, the vector could transfect a $tat_{III}$ cell line such as those described in U.S. patent application Ser. No. 806,263, now U.S. Pat. No. 4,981,790. Alternatively, the transfected cell could be co-transfected with a $tat_{III}$ gene or the $tat_{III}$ gene product could be added to the cells. As a result of the CRS one would obtain large quantities of mRNA for the desired gene, but this gene would not be expressed until the CAR counteracted the effect of the CRS. This anti-CRS effect would not occur until the CAR was exposed to a sufficient amount of the art gene product.

The tat and art sequences from HIV-2, HTLV-IV and STLV-3 are known and vectors containing functional genes can be prepared by the person of ordinary skill in the art based upon the present disclosure when CRS and CAR regions corresponding to these vital genomes are used.

The exposure of the CAR to the art gene product can occur by a variety of mechanisms. For example, one could add the art gene product directly to the cell's culture medium at a desired preselected time. Alternatively, the art gene may be under the control of a secondary factor and not "turned on" until a desired preselected time. Such an art gene can already be present in the cell by use of an art cell line or it can be on the vector. The secondary factor can, for example, be temperature dependence and not express the protein until a certain temperature is reached or chemical dependence such as a hormone. Alternatively, at a desired preselected time, one can transfect the cell with a vector containing the art gene or cocultivate transfected cell with an art cell line. See U.S. patent application Ser. No. 865,151, now U.S. Pat. No. 4,935,372.

Upon exposure to a sufficient amount of the art gene product the CAR represses the inhibitory effect of the CRS and the desired protein would be expressed rapidly. Because high levels of mRNA have already been built up one can obtain expression of the desired gene product in high levels in a short period of time. Very high levels of protein production result when this expression is carried out under the direction of an HIV-I LTR in the presence of the $tat_{III}$ gene product. Thus, problems encountered with the expression of heterologous genes such as cell death or enzymatic attack on the heterologous protein can be minimized. Further, by using discrete CRS and CAR sequences, the creation of env (and/or gag)-desired gene product fusion proteins can be avoided.

Although not wishing to be bound by theory, the existence of cis-acting inhibitory and art-responsive sequences within the envelope gene can explain art dependence of gag and env gene expression. The CRSs within the ARE region could suppress the expression of both the gag and env proteins as both of the mRNAs from which these proteins are synthesized contain $CR5_{1,2,3}$, and $_4$. The expression of the gag and env genes could be relieved by CAR sequences in the presence of the art product. We believe similar regulatory sequences exist within other HIV coding regions, for example, within the gag and pol genes. It is possible that some of the regulatory effects reported here are evident only when used in heterologous gene assays. However, we consider this unlikely as regulation of the CAT and hGH genes closely mimics that of the gag and env genes.

In the assays used here, the phenotype of the CAR is to relieve the effect of CRS, as no significant additional increase on heterologous gene expression is observed in the presence of the are gene product for those plasmids that lack the HIV-I CRS. The existance of intragenic cis-acting regulatory sequences is not without precedent. For example, sequences within the gag gene of Rous sarcoma virus function as enhancer elements [Arrigo et al., *Mol. Cell. Biol*, 2:388–397 (1987)]. However, our results demonstrate that the CAR sequences do not have properties characteristic of transcriptional enhancer elements. The activity of the $CAR_2$ sequence appears orientation dependent as revealed by the plasmid pair pAR-1SV/pAR-1SVR. Furthermore, the CAR sequences do not substitute for enhancer elements for the HTLV-I promoter in either the presence or absence of art.

The regulatory pathway described by the art-ARE system permits differential utilization of messages for regulatory and virion structural proteins. We have shown that the CRS plays an important role in this regulation to inhibit gene expression in cis. In the absence of the CAR sequences, the inhibitory effects of the CRS sequences are profound and are not affected by the art product. The CRS sequences may serve to block translation of mRNAs or may destabilize the mRNAs. The existence of sequences that decrease the half life of mRNA has recently been reported [Kamen et al., *Cell* 46:659–667 (1986)]. Introduction of a 51 nucleotide AT-rich sequence derived from a 3' non-coding region from a human lymphokine gene, GMCSF, into the 3' untranslated region of the rabbit betaglobin gene significantly shortens the half life of the betaglobin mRNA [Kamen et al., supra). It is possible that the sequences within the CRS region described herein confer a similar activity. Placing a CAR sequence into the 3' untranslated region along with a cis-acting regulatory sequence, for example, this GMCSF cis-acting sequence should counteract the GMCSF cis-acting inhibition in the presence of art protein. The existence of intragenic transcriptional termination sequences has also been reported [Johnson et al, *Mol. Cell. Biol.* 6:4008–4018 (1986)]. However, we do not consider it likely that the CRSs function as a transcriptional terminator as the tat product is made from a spliced transcript derived from a full length species of the proviruses, and the expression of tat is not dependent on art.

Differential expression of virion structural and regulatory genes may play an important role in the establishment of viral latency by permitting expression of regulatory genes in the absence of the expression of viral gene products such as env that are lethal to T4+ lymphocytes. Differential expression of regulatory and structural genes may also play a role in the lytic cycle, by permitting the accumulation of gene products such as $tat_{III}$ to accumulate prior to the synthesis of the gag and env gene products.

These sequences also permit research into a method whereby the CAR sequence can be inactivated. Such a result could prevent the expression of the structural gene product and maintain the virus in a latent period.

The present invention can also be used to create a live attenuated vaccine. By using a provirus in which all the CAR regions are removed, but not the CRS, the virus can produce the regulatory proteins but not the structural proteins and is thus not able to cause the disease. However, it is possible to generate an antigenic response to the regulatory protein.

The present invention is further illustrated by the following examples. These examples are provided to aid in understanding of the invention and are not to be construed as a limitation thereof.

EXAMPLES

Cell Lines

Jurkat $tat_{III}$ cells were grown in RPMI-1640 medium supplemented with 10% fetal bovine serum. Hela $tat_{III}$ and CHO $tat_{III}$ cells were grown in Dulbecco modified Eagles' medium (DME) supplemented with 10% fetal bovine serum. Stable expresison of the $tat_{III}$ gene was achieved by infection of Jurkat, HeLa, and CHO cells with a defective amphotropic retroviral $tat_{III}$ expression vector by the method taught in U.S. patent application Ser. No. 806,263, now U.S. Pat. No. 4,981,790 [See also Rosen et al., *Nature* 319:555–559 (1986)]. The retroviral vectors used for establishment of these cells lines do not contain an intact art gene and as such are incapable of art expression. Stable expression of $tat_{III}$ in the Jurkat $tat_{III}$ and CHO $tat_{III}$ cell lines used here was achieved by infection with an amphotropic retroviral $tat_{III}$ cDNA expression vector using standard techniques. This vector was constructed by inserting the $tat_{III}$ cDNA fragment [Arya et al., supra) into the Bam Hi site of plasmid pZIP-NEOSV(x)i [Cepko et al., *Cell* 37:1053–1062 (1984)]. The presence of a functional tat product in these cell lines was confirmed by demonstration of increased levels of HIV-I LTR directed CAT gene expression relative to that obtained in the tat minus cell lines. The $tat_{III}$ cDNA expression vector used lacks the second exon of the art gene.

Plasmid Constructions

All DNA manipulatons were essentially performed as described by Maniatis et al (1983). A brief description of each plasmid construct is given below. The nucleotide positions are numbered with respect to the site of RNA initiation, +1. All proviral sequences were obtained from plasmid HXBc2 [Fisher et al., *Nature* 316:262–265 (1985).

(i) pH3-art. The art coding region was obtained from a cDNA clone [Arya et al., supra] by limited digestion with Bal 31 exonuclease [Legarski et al., *Nucleic Acids Res.* 5:1445–1460 (1978)] following cleavage with Sal I. The fragment containing the art coding region was cloned into a Sp64 multiple restriction enzyme linker (Promega Biotech) present between HIV-I LTR nucleotides −167 to +81 and SV40 polyadenylation signals obtained from the Bgl II-EcoRI fragment of plasmid pSV2-β [Mulligan et al., *Nature* 277:108–114 (1977)]. pH3-art is shown in FIG. 4A. The boundaries of the art gene were discovered based upon the observation that mutations located both 5' to the env gene and within a 3' portion of the env gene give a similar phenotype with respect to gag and env gene expression. The art gene consists of two coding exons which partly overlap the first and second exons of $tat_{III}$, in an alternative reading frame. Beginning with a methionine codon at position 5550, the first exon extends to a known splice donor site at nucleotide 5625 and the splice acceptor at nucleotide 7956 precedes an in-frame open reading frame ending with a stop codon at nucleotide 8277. In this experiment, cDNA from HIV-I (as disclosed by Araya et al., supra, although any source of HIV-I cDNA can be used) containing both the $tat_{III}$ and art coding sequences was treated with Bal 31 exonuclease to remove the $tat_{III}$ ATG codon present 5' to the predicted art initiator codon. The cDNA fragment containing the intact art coding region and lacking the $tatii_{I}$ ATG codon was subcloned into a standard transient expression vector, pH3. This vector contains a portion of the HIV-I LTR, including the enhancer, promoter, and TAR sequences (sequences responsive to tat) and polyadenylation signals obtained from SV40 virus. Shown at the bottom are the sequences present in pH3-art. To achieve a high level of art gene expression, transient expression experiments were performed in Jurkat cells that constitutively express the $tat_{III}$ product but are unable to synthesize the art gene product [U.S. patent application Ser. No. 865,151, now U.S. Pat. No. 4,935,372; Rosen et al., *Nature* 319, supra]. The activity of pH3-art was assessed by examining its ability to complement gag and env gene expression following co-transfection with an art negative provirus, HXBc2-Bfs [Sodroski et al., *Nature* 321:412–417 (1986)]. See FIG. 4B In a control experiment, HXBc2-Bfs was co-transfected with plasmid pEx5496 venv that expresses art from a genomic DNA fragment [U.S. patent application Ser. No. 865,151, now U.S. Pat. No. 4,935,372]. Forty-eight hours following co-transfection with the plasmid DNAs indicated, gag and env gene proteins were immunoprecipitated from cell lysates using AIDS patient antiserum. The virion env (gp160) and capsid (p55) proteins are shown.

(ii) HIV-I and HTLV-I LTR/CAT/HIV Hybrid Constructs. See FIG. 3A. A CAT gene fragment containing a Bgl II restriction site (a gift from D. Celander) [See also Gorman, C. M. et al, *Mol. Cell Biol.* 2:1044–1051 (1982)] following the stop codon and preceding the polyadenylation signal was treated with DNA polymerase I following cleavage with Bg II and ligated to synthetic Sal I linkers. After cleavage with Hind III and Sal I, the poly A-CAT gene fragment was cloned into the Hind III-Sal I, the poly A-CAT gene fragment was cloned into the Hind III-Sal I site of an Sp64 (Promega Biotech) multiple restriction polylinker that was present 3' to HIV-I LTR sequences −167 to +81. Thus, the resultant plasmid, pIII, contains an HIV-I LTR 5' to a CAT gene that lacks polyadenylation sequences. To incorporate HIV-I sequences 3' to the CAT gene, a Sal I-Xba 1 fragment encompassing HIV-I nucleotides 5462 to 9177 was cloned into the Sal I-Xba I sites present 3' to the CAT gene present in plasmid pIII. The Sal I-Xba I proviral segment was obtained from a clone that contained a frameshift mutation at the Bam Hi site within the second coding exon of art and a deletion of the 5' end of the first coding exon of tat [Sodroski et al., Nature 321:supra]. Deletion of intragenic sequences from pIIIAR to generate $p_{III}\Delta ST$ was accomplished by digestion using standard techniques with Kpnl followed by recirculization to reform the deleted plasmid. Plasmids pI, pI AR, and pIΔAR are identical to their respective HIV/CAT hybrid constructs pIII, pIIIAR and pIIIΔAR except for replacement of the HIV-I 5' LTR with HTLV-I LTR sequences (nucleotides −350 to +325) obtained from plasmid pU3R-I.

Figures 3A, 3B:
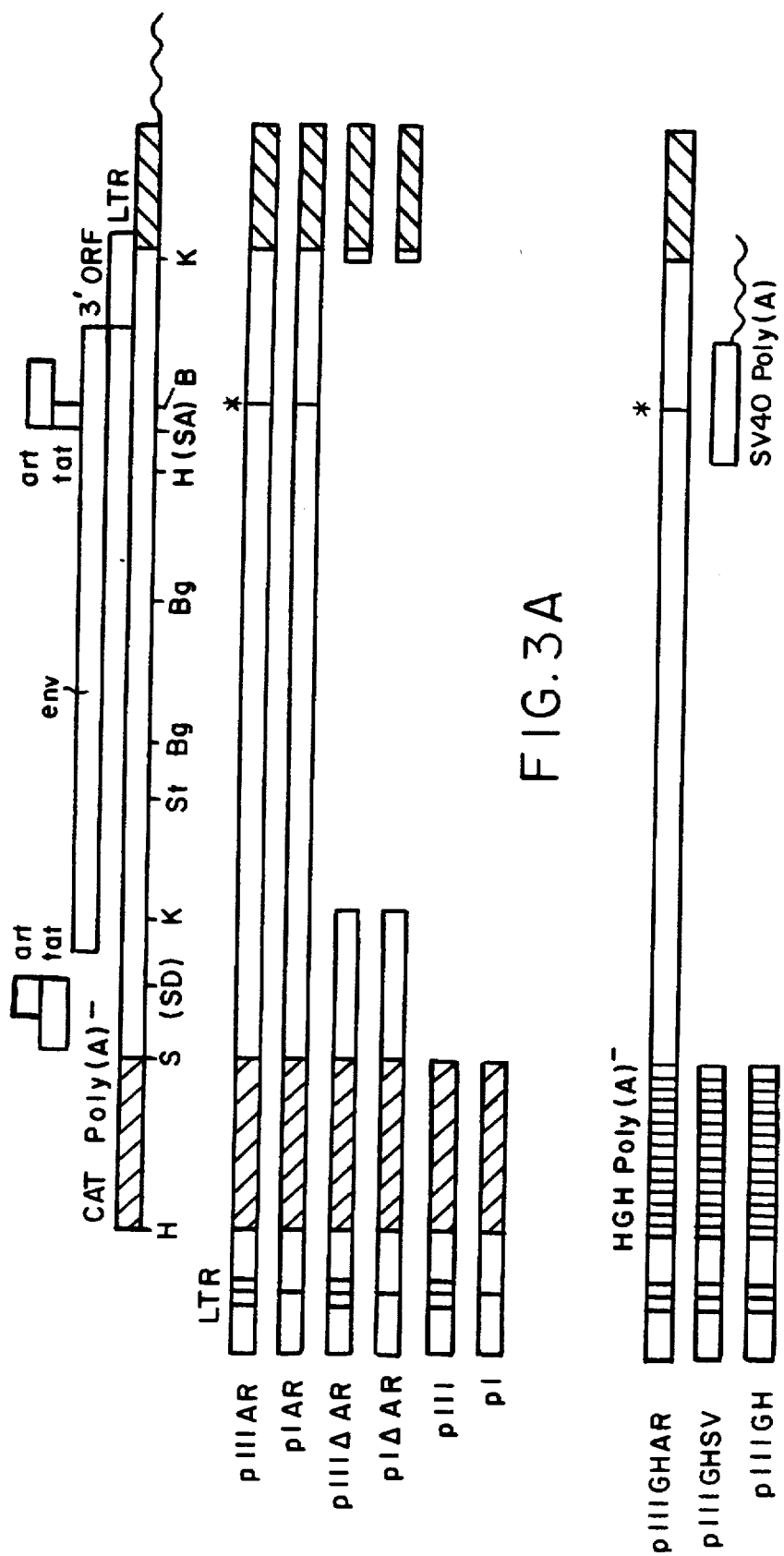
FIG. 3A is an illustration of the structure of the hybrid HIV/CAT constructs.
FIG. 3B is an illustration of the structure of the hybrid HIV-human growth hormone (hGH)/HIV constructs.

FIG. 3A is a schematic representation indicating the origin of the proviral sequences present in each hybrid construct. The 5' end of the CAT gene is flanked by either HTLV-I or HIV-I LTR sequences as indicated. The indicated HIV-I sequences and poly A sequences were subcloned 3' to the CAT gene (striped box) that contains a stop codon but lacks polyadenylation sequences. Polyadenylation signals were provided from a 3' HIV-I LTR (solid box). The abbreviations used for restriction enzyme sites are: H, Hind III; S, Sal l; K, Kpnl; ST, Stul: Bg, Bgl II; B, Bam HI. SD and SA indicate the position of the known splice donor and acceptor junctions, respectively, [Muesing et al., Nature 313:450–447 (1985); Arya et al., supra)].

(iii) Deletion series of the HIV insert in plasmid pIIIAR.

Figure 6A:
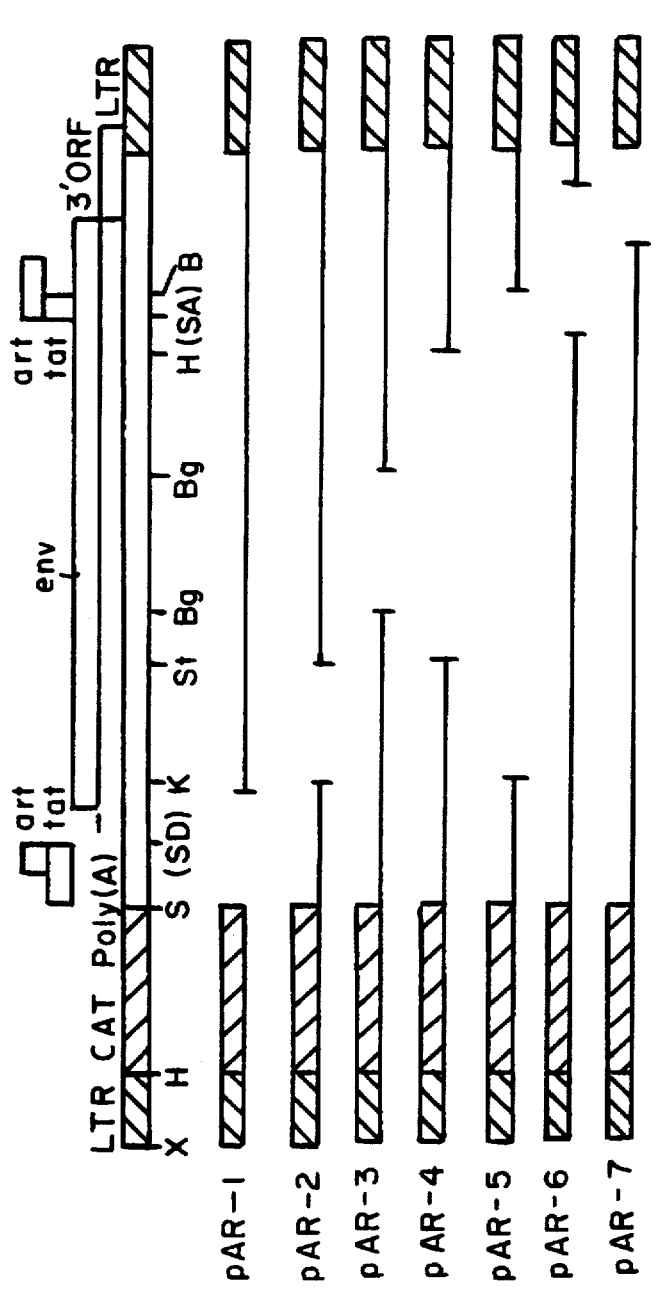
FIG. 6A is a schematic representation showing the relative position of deletions within the HIV-I sequences in plasmid pIIIAR.

Internal deletions within the HIV-I proviral sequences present within plasmid pIIIAR were made using either limited digestion with Bal 31 exonuclease (Legarski et al., supra) or available restriction enzyme sites. The termini of each deletion were determined by DNA sequence analysis as described by Maxam and Gilbert, P.N.A.S. (USA) 74:560–564 (1977). The 5' and 3' border, respectively, of the deleted proviral sequences in the plasmids shown in FIG. 3A is given below. pAR-1 deletes nucleotides 5432 to 5893; pAR-2 deletes nucleotides 5893 to 6376; pAR-3 deletes nucleotides 6583 to 7163; pAR-4 deletes nucleotides 6376 to 7683; pAR-5 deletes nucleotides 5893 to 8020; pAR-6 deletes nucleotides 7761 to 8235; pAR-7 deletes nucleotides 8204 to 8560. (See FIG. 6A) Plasmids pAR-1SV, pAR-2SV and pAR-3SV (FIG. 6B) contain SV40 polyadenylation signals at HIV-I nucleotide 8561. Each plasmid contains an internal deletion of HIV-I nucleotides 7163 to 7683. Additional deletions encompass nucleotides 7236 to 6536, plasmid pAR-2SV, or nucleotides 5893 to 6536, plasmid pAR-3SV. Plasmid pAR-1SVR is identical to pAR-1SV except for inversion of the HIV-I Kpn fragment present in pAR-1SV.

FIG. 6 is a schematic representation showing the relative position of these deletions within the HIV-I sequences present in plasmid pIIIAR. The plasmids shown in 5B lack a 3'LTR (solid box) and contain SV40 polyadenylation sequences (speckled box) derived from the early region of SV40. The abbreviations used for restriction enzyme sites are the same as those used for FIG. 3.

(iv) 5' deletions series of HIV-I insert in pA-6376. Plasmid pA-6376 contains HIV-I nucleotides 6376 to 7761 present between HIV-I LTR CAT sequences and SV40 polyadenylation sequences. The constructs shown in FIG. 8A were generated by treating pA-6376 with Bal 31 exonuclease following cleavage with Sal I (nucleotide 6376).

Figure 8:
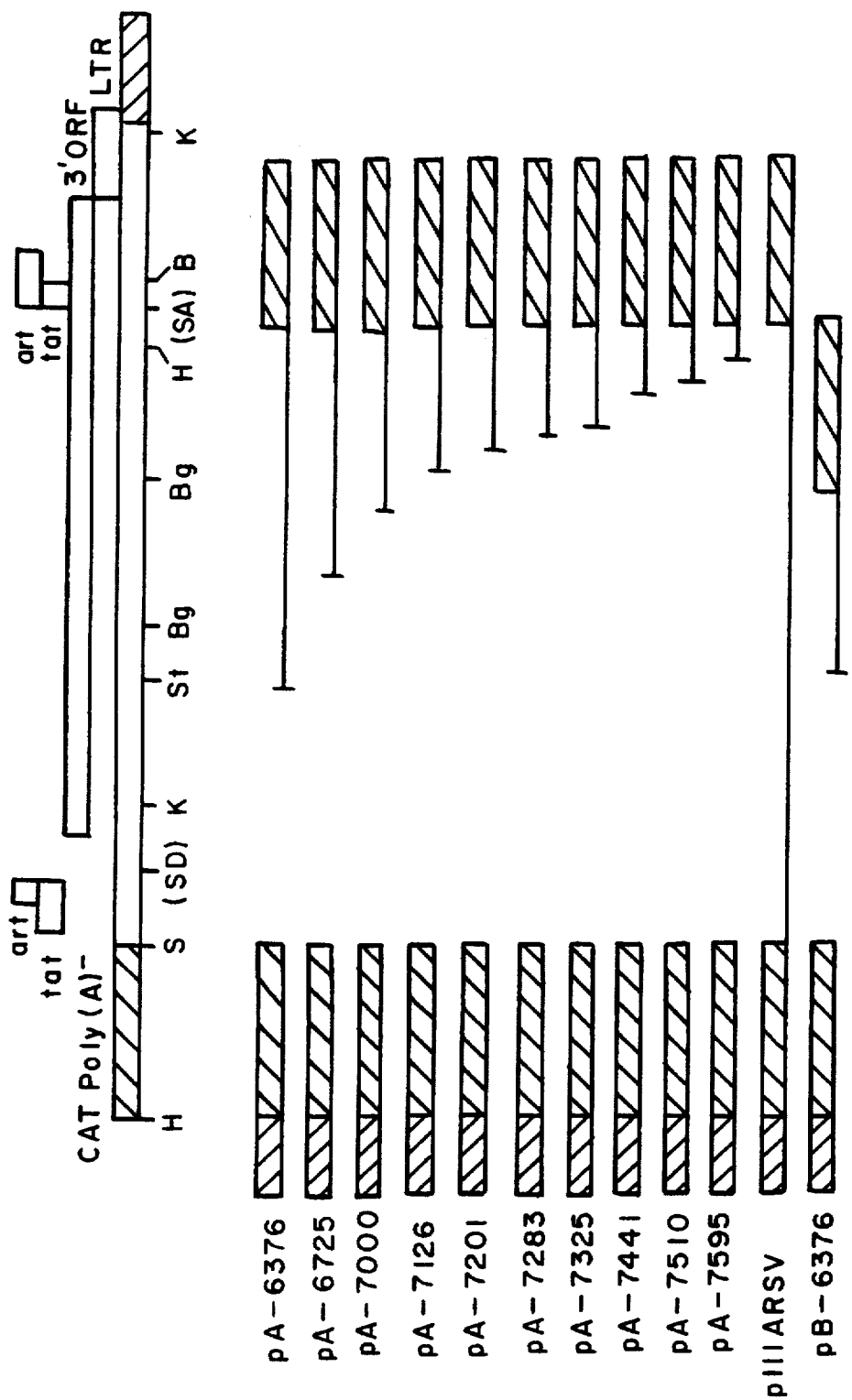
FIG. 8 is a schematic representation of 5' deletions made within HIV-I nucleotide sequences 5332–7760.

The overlapping ends of the restriction fragment were filled out with T4 DNA polymerase and ligated to synthetic Cla I linkers. Following cleavage with Cla I and Xho I, an intact LTR—CAT gene was recloned into each deletion plasmid by standard techniques. The 5' border of each construct was confirmed by DNA sequence analysis. The name of each plasmid is indicative of the 5' most HIV-I nucleotide present in each. FIG. 8 is a schematic representation of these constructs. The 3' border of each clone lies at HIV-I nucleotide 7760. HIV-I LTR sequences (solid box), CAT gene sequences (striped box), HIV-I intragenic sequences (single line) and SV40 polyadenylation signals (speckled box) are shown. The abbreviations used for restriction enzymes sites are the same as used for FIG. 3.

(v) HIV-I LTR/Human Growth Hormones Hybrid Plasmids. The human growth hormone (hGH) gene was obtained from an hGH cDNA fragment present in plasmid pc.hGH800 (a gift from Dr. Norman Eberhardt although any known source of the hGH gene can be used). To remove polyadenylation signals, plasmid pc.hGH800 was first cleaved at the Sma I site present 8 nucleotides 3' to the stop codon. The Sma I site was then converted to a Sal I site and a Hind Ill Sal I fragment that contained the hGH coding sequences was cloned 3' to the HIV-I LTR/CAT gene fragment that was used to construct plasmid pill (see above). The LTR/hGH sequences on the resultant plasmid pIIIGH, were used to replace the HIV LTR/CAT sequences present on plasmid pIIIAR to yield PIIIGH-AR. Plasmid pIIIGH-SV contains SV40 polyadenylation sequences 3' to the hGH fragment present in plasmid pIIIGH. These constructs are shown in FIG. 3B.

(vi) Enhancer test plasmids. HIV-I nucleotides 6970 to 8440 (pC-55/III 1470) and 5963 to 8442 (pC-55/2479) were cloned in the orientation shown in FIG. 9 into a multiple restriction site polylinker (Promega Biotech) that was present 5' to HTLV-I LTR sequences −55 to +325 [Rosen et al., P.N.A.S. 82:6502–6506 (1985)]. The HTLV-I LTR sequences present on the parental vector plasmid, pC-55, have previously been shown to be responsive to heterologous enhancer elements [Rosen et al., supra; Rosen et al., J. Virol. 157:379–384 (1986); see also U.S. patent application Ser. No. 614,297, now U.S. Pat. No. 4,738, 922]. The HTLV-I LTR sequences present between nucleotides −55 to +325 are responsive to cis-acting enhancer elements. Plasmid pC-55/III 2479 and pC55/III 1470 contain 2479 and 1470 HIV-I nucleotides, respectively, cloned in the orientation shown in FIG. 9.

(vii) 5' env and gag gene hybrid constructs. To construct plasmids plenv-317, plenv-314, and plenv-100, a Hind III—Kpn I HIV-I proviral fragment encompassing nucleotides 5572 to 5893 was cloned into an Sp64 polylinker present 3' to HIV-I LTR sequences −167 to +81. Deletions were generated by digestion with Bal 31 exonuclease following cleavage with Kpn I (nucleotide 5893). DNA termini were filled out with T4 DNA polymerase, ligated to Kpn I linkers then cleaved with Kpn I and Bam HI. The linearized DNA was then ligated to a Kpn I—Bam HI segement of DNA that contained the CAT gene and SV40 polyadenylation sequences. The number and the name of each plasmid indicates the number of HIV-I nucleotides present 3' to nucleotide 5572. Plasmids pLgag-404 and pLgag-321 were constructed by subcloning a Hind III fragment of plasmid HXBc2 (nucleotides 81 to 630) into the Hind III site of plasmid pU3R-III. To generate deletions, plasmid DNA was treated with Bal 31 exonuclease following cleavage at the EcoRI site that was within the CAT gene. The resultant LTR/leader fragments were then subcloned adjacent to an intact CAT gene.

DNA Transfections, CAT and hGH Assays

Adherent cells were transfected with 0.5 to 1.0 µg of CsCl banded indicator plasmid DNA. Lymphoid cells were transfected with 3 µg of DNA. Co-transfections were performed with either 3 µg of pH3-art or 3 µg of control DNA [plasmid pU3R-IIIβ; Rosen et al., *Cell* 41:813–823 (1985)]. A DNA dose response assay was done for each cell line using plasmid pIIIAR. The final amount of DNA chosen for each transfection was an amount that gave a linear response in the dose response assay (Data not shown). Transfections were performed using the DEAE dextran technique as described by Lopata et al., *Nucl. Acids Res.* 12:5707–5717 (1984)., (adherent cells) and Queen and Baltimore *Cell* 33:741–748 (1983), (lymphoid cells). CAT assays were performed 48 hours post-transfection as described previously (Gorman et al., supra). The amount of $^{14}C$-chloramphenicol converted to acetylated products was determined by liquid scintillation counting of the spots cut out from the thin layer chromatography plate.

For hGH assays, medium obtained (100 µl) from cells 48 hours post-transfection was used to measure the level of secreted human growth hormone. The levels of hGH levels were determined using a known hGH radioimmune assay kit (Nichols Institute, San Juan Capistrano, Calif.).

Immunoprecipitations

Jurkat tat$_{III}$ cells (1×10$^7$) were transfected with 5 µg each of the individual plasmid DNAs. Approximately 40 hours post-transfection cells were metabolically labelled with $^{35}S$-cysteine for an additional 8 to 12 hours. Cell lysates were prepared and HIV-specific proteins were immunoprecipitated with AIDS patient antisera as described in [Goh et al., *J. Virol.* 59:181–184 (1986). Immunoprecipitable products were resolved using SDS polyacrylamide gel electrophoresis (Laemmli, et al., *Nature* 227:680–685 (1970).

Regulation of Heterologous Gene Expression by the Art Gene Product

The 3' half of an infectious HIV-I provirus, was placed 3' to the bacterial chloramphenicol acetyltransferase (CAT) gene as described above (FIG. 3A). In this context the HIV-I sequences are incorporated within the non-coding portion of the CAT gene transcript. The segment of the provirus was derived from an art-defective mutant that contained a frameshift mutation in the 3' coding exon of the art gene as disclosed in U.S. patent application Ser. No. 865,151, now U.S. Pat. No. 4,935,372. Expression of the CAT gene was directed by the HIV-I long terminal repeat (LTR) sequences −167 to +81. A control plasmid that contains the HIV-I LTR and CAT gene 5' to SV40 polyadenylation signals was also used for the experiments (plasmid pU3R-III; see Sodroski et al., *Science* 227:171–173 (1985)).

Figure 4A:
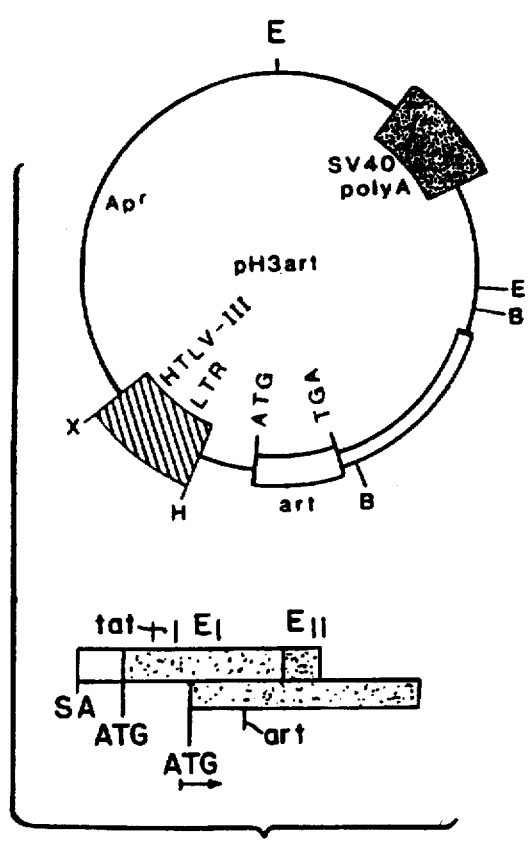
FIG. 4A shows the construction of plasmid pH3-art and the sequences present in pH3-art.
Figure 4B:
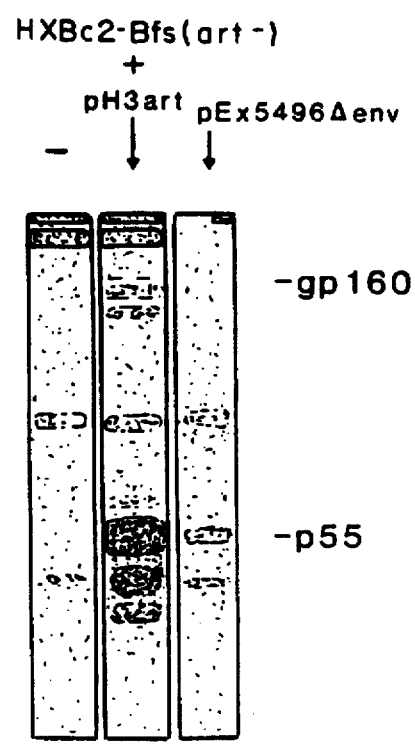
FIG. 4B shows the activity of plasmid pH3-art.

A plasmid (pH3-art) was constructed designed to express the art gene product as described above (FIG. 4A). The ability of this plasmid to complement the defect in gag and env synthesis of an art defective provirus was analyzed in co-transfection experiments (FIG. 4B). No detectable gag or env gene products were detectable following co-transfection of susceptible cells with plasmid pHXBc2-Bfs that contains a frameshift mutation in the art gene. However, co-transfection of plasmid pHXBc2-Bfs with plasmid pEx5496 env previously shown to express the art function [U.S. patent application Ser. No. 856,151, now U.S. Pat. No. 4,935,372; Sodroski et al., *Nature* 321: supra], or pH3-art results in the synthesis of both gag and env gene proteins (FIG. 4B). These experiments demonstrate that plasmid pH3-art expresses a functional art gene product. This plasmid does not express the tat gene product or any other known viral gene protein products.

Cell lines were transfected with the hybrid HIV/CAT constructs described above in the presence or absence of the pH3-art plasmid. To obtain high levels of HIV LTR directed art gene expression, cell lines (HeLa tat$_{III}$, Jurkat tat$_{III}$ and CHO tat$_{III}$) that constitutively express the tat$_{III}$ gene were used for these experiments [Rosen et al., *Nature* 319, supra (1986)]. The level of CAT enzyme activity was measured as discussed above 48 hours post-transfection.

Figure 5A:
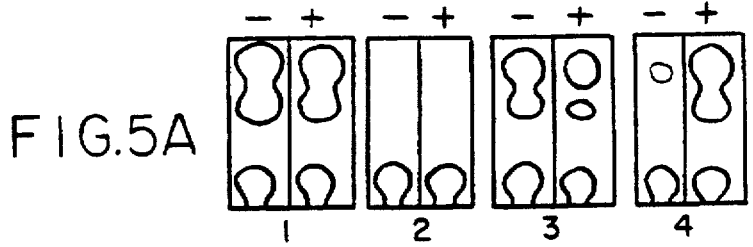
FIGS. 5A and B show the effect of the art gene product on CAT expression in Jurkat tat-III directed by various hybrid-HIV/CAT constructs.
Figure 5B:
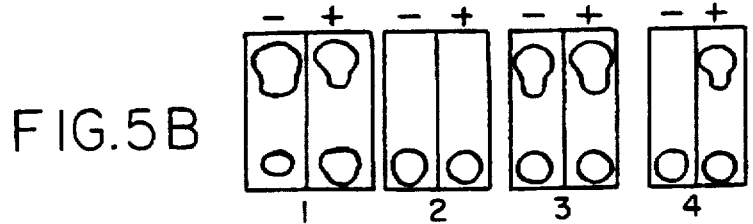

High level expression of the CAT gene was detected in all cells transfected with plasmid pU3R-III (Table 1, FIG. 5).

TABLE 1

Expression of hybrid HIV/CAT gene constructs in the presence and absence of the Ia protein
CAT Activity$^a$

| Experiment | Plasmid pH3-art$^b$ | HeLa-tat-III | | | Jurkat-tat-III | | | CHO-tat-III | | |
|---|---|---|---|---|---|---|---|---|---|---|
| | | − | + | ( )$^c$ | − | + | ( )$^c$ | − | + | ( )$^c$ |
| 1 | pU3R-III | 3.16 | 2.91 | (0.9) | 1.93 | 1.86 | (1.0) | 1.86 | 2.21 | (1.2) |
| | pIIIAR | 0.13 | 3.90 | (30) | 0.02 | 0.53 | (26) | 0.30 | 1.46 | (49) |
| | pIIIΔAR | 1.67 | 1.72 | (1.0) | 1.41 | 1.36 | (1.0) | | | |
| | pIII | <.01 | <.01 | | <.01 | <.01 | | | | |
| 2 | pU3R-1 | 6.41 | 5.6 | (0.9) | 5.06 | 1.78 | (0.4) | | | |
| | pIAR | 0.04 | 1.26 | (32) | 0.06 | 0.77 | (13) | | | |
| | pIΔAR | 4.06 | 4.66 | (1.1) | 2.53 | 1.20 | (0.5) | | | |
| | pI | <.01 | <.01 | | <.01 | <.01 | | | | |
| 3 | pU3RIII | 3.06 | 2.40 | (0.8) | 1.20 | 1.14 | (0.9) | 6.60 | 5.50 | (0.8) |
| | pIIIAR | 0.10 | 2.40 | (24) | 0.04 | 1.36 | (34) | 0.23 | 5.80 | (25) |
| | pAR-1 | 0.03 | 0.36 | (12) | <.01 | 0.40 | | | | |

TABLE 1-continued

Expression of hybrid HIV/CAT gene constructs in the presence and absence of the la protein
CAT Activity[a]

| Experiment | Plasmid pH3-art[b] | HeLa-tat-III | | | Jurkat-tat-III | | | CHO-tat-III | | |
|---|---|---|---|---|---|---|---|---|---|---|
| | | − | + | ( )[c] | − | + | ( )[c] | − | + | ( )[c] |
| | pAR-2 | 0.16 | 2.63 | (16) | 0.03 | 0.80 | (27) | | | |
| | pAR-3 | 1.20 | 3.21 | (2.7) | 0.24 | 2.21 | (9.2) | | | |
| | pAR-4 | 0.12 | 0.15 | (1.2) | 0.27 | 0.24 | (0.9) | | | |
| | pAR-5 | 1.70 | 2.20 | (1.3) | 0.41 | 0.46 | (1.1) | | | |
| | pAR-6 | 0.12 | 2.22 | (19) | 0.05 | 1.93 | (39) | | | |
| | pAR-7 | 1.84 | 4.64 | (2.5) | 0.83 | 4.30 | (5.2) | | | |
| | pAR-1SV | 0.05 | 1.50 | (30) | 0.06 | 0.54 | (9.0) | 0.41 | 6.71 | (16) |
| | pAR-2SV | 0.08 | 1.80 | (23) | 0.13 | 1.43 | (11) | 0.26 | 5.72 | (22) |
| | pAR-3SV | 0.32 | 2.30 | (7.2) | 0.52 | 3.51 | (6.7) | 1.10 | 8.12 | (7.4) |
| 4 | pU3R-III | 2.66 | 2.53 | (0.9) | | | | 1.86 | 1.53 | (0.8) |
| | pIIIAR | 0.08 | 1.80 | (23) | | | | 0.05 | 1.40 | (28) |
| | pIIIARSV | 0.59 | 1.26 | (2.1) | | | | 0.53 | 0.86 | (1.6) |
| | pA-6376 | 0.03 | 0.46 | (15) | | | | 0.03 | 0.36 | (12) |
| | pA-6725 | 0.71 | 3.40 | (4.8) | | | | 0.31 | 1.86 | (6.0) |
| | pA-7000 | 0.68 | 3.70 | (5.4) | | | | 0.34 | 1.76 | (5.2) |
| | pA-7126 | 0.66 | 2.40 | (3.6) | | | | 0.80 | 3.60 | (4.5) |
| | pA-7201 | 0.26 | 2.06 | (8.0) | | | | 0.24 | 2.46 | (10) |
| | pA-7205 | 0.46 | 2.26 | (5.0) | | | | 0.31 | 2.80 | (9.0) |
| | pA-7283 | 0.24 | 0.80 | (3.3) | | | | 0.33 | 1.55 | (4.6) |
| | pA-7325 | 1.00 | 1.00 | (1.0) | | | | 0.86 | 0.78 | (0.9) |
| | pA-7441 | 1.13 | 0.80 | (0.7) | | | | 0.72 | 0.78 | (1.1) |
| | pA-7510 | 1.00 | 1.12 | (1.1) | | | | 1.28 | 0.93 | (0.7) |
| | pA-7595 | 0.56 | 0.46 | (0.8) | | | | 0.46 | 0.51 | (1.1) |
| | pB-6376 | 0.46 | 0.38 | (0.8) | | | | 0.43 | 0.41 | (0.9) |

[a]Cells were transfected with 1 μg (HeLa tat$_{III}$ and CHO tat$_{III}$) or 3 μg (Jurkat tat$_{III}$) of the indicated plasmid DNA. The amount of DNA used was determined from a DNA dose response curve made for each cell line. The absolute CAT activity was determined by liquid scintillation counting of the spots cut from a thin layer chromatogoraphy plate. The percent conversion per minute of chloramphenicol to its acetylated forms is given. The results shown for each group of experiments (1–4) were all done on the same set of cells on the same day. Each experiment was repeated at least two times. The results reported represent the levels of CAT activity obtained in a single experiment. Although the absolute levels of CAT activity varied up to 2 fold from experiment to experiment, the relative differences in CAT activity directed by the plasmids varied no more than 20% from experiment to experiment.
[b]The plasmids indicated were co-transfected with 3 μg of plasmid pH3-art (+) or an equivalent amount of non-specific competitor DNA (plasmid pU3R-III P; Rosen et al., Cell 41:813–823 (1985)).
[c]The induction value given in parenthesis was determined by dividing the percent CAT activity obtained in the absence of art by the percent CAT activity obtained in the presence of art FIG. 5 shows the effect of the art gene product on CAT gene expression directed by the hybrid HIV/CAT constructs. Jurkat-tat$_{III}$ cells were transfected with 3 μg of each hybrid plasmid in the presence (+) and absence (−) of plasmid pH3-art. The amount of DNA used for transfection was within the linear range as determined from a DNA dose response curve. CAT assays were performed forty-eight hours post-transfection as described in experimental procedures. Shown are autoradiograms of CAT assays obtained from time points within the linear range of a time course assay. The time points chosen are the same for each pair of assays. FIG. 4A shows CAT assays of Jurkat-tat$_{III}$ cells transfected with plasmids pU3R-III (lane 1); pIII (lane 2); pIIIΔAR (lane 3); pIIIAR (lane 4). FIG. 4B shows CAT assays of Jurkat-tat$_{III}$ cells transfected with plasmids, pU3R-I (lane 1); pI (lane 2); pIΔAR (lane 3); and pIAR (lane 4). For the experiments shown in FIG. 4B, cells were simultaneously transfected with 3 μg of a plasmid pItat, that expresses the HTLV-I transactivator product.

Expression of the CAT gene was dependent upon the presence of a polyadenylation signal as no detectable enyzmatic activity was observed in cells transfected with plasmid pIII that contains the HIV-I LTR and CAT gene only. The level of CAT activity expressed by these plasmids was unaffected by co-transfection with the pH3-art plasmid. The level of CAT enzyme activity expressed by plasmid pIIIAR in which the 3' portion of the HIV-I provirus is located 3' to the coding sequence of the CAT gene was markedly reduced as compared to the level detected upon transfection of the same cells with plasmid pU3R-III. However, co-transfection of pIIIAR with plasmid pH3-art that expresses the art protein increased the level of CAT gene expression substantially (26 to 49 fold). In the presence of art, the level of CAT enzyme directed by plasmid pIIIAR was approximately equal to that obtained with plasmid pU3R-III in HeLa tat$_{III}$ cells but was somewhat lower in the Jurkat tat$_{III}$ and CHO tat$_{III}$ cells. This indicates that the 3' half of the virus possesses sequences that negatively regulate CAT gene expression and this inhibitory effect can be overcome by the product of the art gene. These results also indicate that neither tissue nor species specific factors are required for the regulatory effects of the 3' proviral sequences or for art gene function.

The generality of the results obtained with the CAT gene was demonstrated by measuring the effect of the 3' proviral sequences on a second heterologous gene, the gene that encodes the human growth hormone (hGH) [Selden et al., Mol. Cell. Biol. 6:3173–3179 (1986)]. The cDNA sequences encoding the hGH gene were inserted between the HIV-I LTR sequences and the 3' end of the HIV-I provirus (plasmid pIIIGHAR; FIG. 3B). The hGH sequences used for this plasmid are devoid of the cellular hGH promoter and polyadenylation sequences. Two additional plasmids were made, one that contained the human growth hormone gene located 3' to the HIV-I LTR with no polyadenylaton signals (pIIIGH) and a second that contained SV40 polyadenylation sequences 3' to the hGH gene (pIIIGHSV). The data of Table 2 shows that the pIIIGHSV plasmid directed the synthesis of hGH in both the HeLa tat$_{III}$ and CHO tat$_{III}$ cells. No significant hGH activity was detected in cells transfected with plasmid pIIIGH. The level of hGH activity directed by these plasmids was not affected by co-transfection with plasmid pH3-art.

TABLE 2

Expression of hybrid HIV/human growth hormone gene constructs in the presence and absence of the art protein.

| | | Secreted hGH (cpm)[a] Cell Line | | | | | |
|---|---|---|---|---|---|---|---|
| | pH3- | HeLa-tat-III | | | CHO-tat-III | | |
| Plasmid | art[b] | − | + | ( )[c] | − | + | ( )[c] |
| pIIIGHSV | | 6826 | 6423 | (0.9) | 13289 | 13567 | (1.0) |
| pIIIGHAR | | 312 | 6083 | (20) | 890 | 9695 | (11) |
| pIIIGH | | 523 | 310 | (0.6) | 163 | 227 | (1.4) |

[a]Cells were transfected with 2 μg of the plasmid DNAs shown in the presence (+) or absence (−) of plasmid pH3-art. At forty-eight hours after transfection, 100 μl of medium was removed and assayed for hGH activity. The counts per minute (CPM) Of $^{125}$I labelled anti-hGH antibody bound to a solid support were corrected by taking the total CPM and subtracting the background CPM obtained from medium of mock transfected cells.
[b]The induction value shown in parentheses represents the value obtained by dividing the corrected CPM obtained in the absence of art by the corrected CPM obtained in the presence of art.

The level of hGH directed by plasmid pIIIGHAR in the absence of the art gene product was very low in both the HeLa tat$_{III}$ and CHO tat$_{III}$ cell lines. Co-transfection of pIIIGHAR with plasmid pH3-art resulted in a marked increase in hGH activity (11 to 20 fold). The level of hGH produced in the presence of the art product by plasmid pIIIGHAR was similar to that obtained with plasmid pIIIGHSV. As was seen for the CAT gene, the 3' half of the HIV-I provirus contains sequences that have an inhibitory effect on the expression of the hGH gene and the repressive effect of these sequences is relieved by the art gene product. Thus, the expression of the CAT and hGH genes linked to the HIV-I provirus sequences mimics the regulation of the gag and env genes themselves.

The Role of the 5' LTR in Art Regulation

Plasmids were constructed in which the 5' HIV-I LTR was replaced with the LTR of the human T lymphotropic virus type I (HTLV-I) (FIG. 3A). For all experiments in which gene expression was driven by the HTLV-I LTR, cells were simultaneously transfected with a plasmid, pItat$_I$, that expresses the trans-activator protein of HTLV-I. The level of CAT enzyme activity directed by plasmid pIΔAR that contains the 3' half of the HIV-I genome located 3' to the CAT gene under control of the HTLV-I LTR was much lower than that of plasmid pU3R-I that contains the polyadenylation sequences of SV40 located 3' to the CAT gene (FIG. 5 and Table 1). However, co-transfection with pH3-art resulted in a marked increase (13–30 fold) in the level of CAT activity directed by plasmid pIAAR. Similar results were obtained using Jurkat cells as recipients. These experiments show that the 5' LTR of HIV-I is not required for the cis-acting repression or cis-acting anti-repression effects exerted by the 3' portion of the HIV-I provirus.

Deletion Mapping of The CRS and CAR

Derivative of the pIΔAR and pIIIΔAR plasmids deleted for a majority of the envelope gene sequences (pIIIΔAR and pIΔAR; FIG. 3B) were constructed and tested for CAT activity in the presence or absence of the are gene product. Deletion of the majority of the env gene resulted in an increased level of CAT gene activity directed by both of these plasmids relative to the respective control plasmids pI AR and pIIIAR (FIG. 5 and Table 1). No increase in enzyme activity was detected upon co-transfection with plasmid pH3-art. Thus, deletion of HIV-I sequences present between nucleotides 5893 to 8561 relieves the inhibitory regulatory effects and eliminates the art responsive anti-inhibitory effect conveyed by the HIV-I sequences.

Figure 6B:
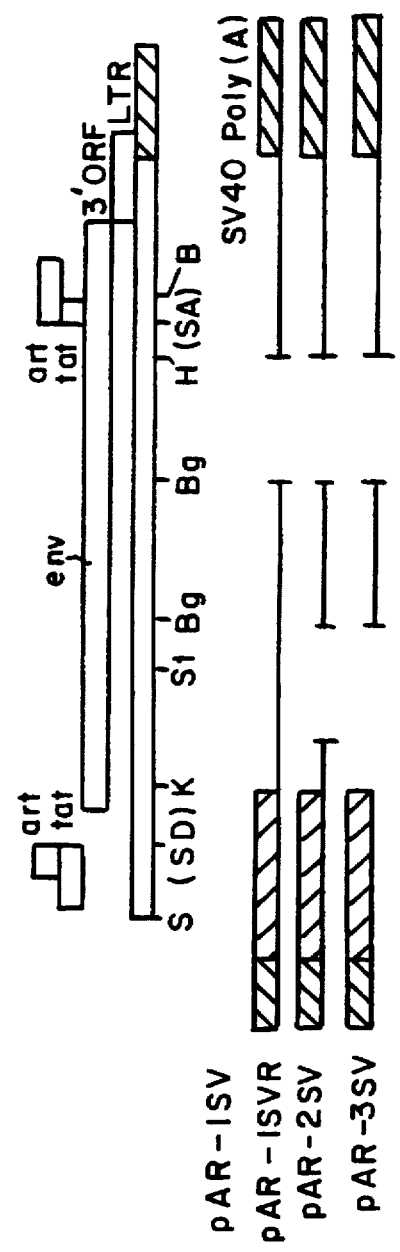
FIG. 6B is a schematic representation showing the relative position of deletions within the HIV-I sequences present in pIIIAR, wherein the plasmid also lacks a 3' LTR and contains an SV40 polyadenylation sequence derived from the early region of SV40.
Figure 7:
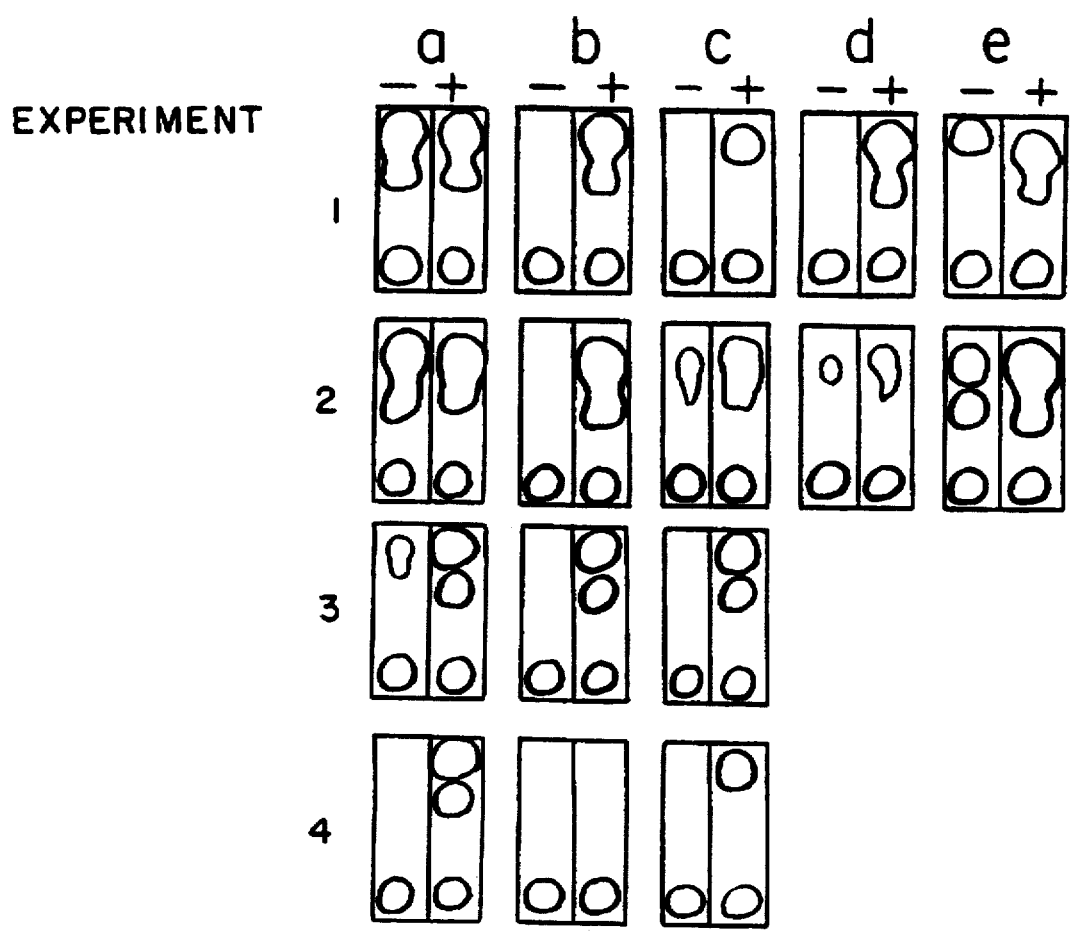
FIG. 7 shows CAT activity of the deletion mutants in the presence or absence of the art gene product.

A series of smaller deletions were also introduced into the proviral sequences present in the pIIIAR plasmid and are represented by the plasmids pAR-1 to pAR-7 (FIG. 6). The level of CAT activity directed by these plasmids was measured in HeLa-tat$_{III}$ cells and Jurkat-tat$_{III}$ cells in the presence or absence of plasmid pH3-art. The effect of these deletions on the level of CAT enzyme activity is shown in FIG. 7 and Table 1. Deletion of the 5' sequences of the provirus segment, a region that includes the 5' coding exons of the tat and art genes, the 5' end of the env gene and the splice donor site of the intron (pAR-1) reduces the level of CAT enzyme activity to about one-third of that seen in the same HeLa tat$_{III}$ cells transfected with plasmid pIIIAR. The level of CAT enzyme activity was increased by at least 12 fold in the presence of art. These results demonstrate that the sequences deleted from the 5' end of proviral insert, including the splice donor site, are not essential for the response of the HIV-I sequences to the art product.

FIG. 7 shows the results of these experiments. Cells were co-transfected with 1 μg of the indicated plasmid DNA plus 3 μg of a non-specific competitor DNA (−) (plasmid pU3R-IIIβ; supra) or 3 μg of pH3-art. (+). CAT assays were preformed 48 hours post-transfection. Autoradiograms shown were obtained from the linear portion of a time course assay. Experiment 1, CHO-tat$_{III}$ cells transfected with plasmid pU3R-III (lane a); pIIIAR (lane b); pAR-1 (lane c); pAR-6 (lane d); and pAR-3 (lane e). Experiment 2. HeLa-tat$_{III}$ transfected with plasmid, pU3R-III (lane a); pIIIAR (lane b); pIIIARSV (lane c); pA-6376 (lane d); and pA-7126 (lane e). Experiment 3. HeLa-tat$_{III}$ cells transfected with plasmids, pU3R-III (lane a); pIIIAR (lane b); and pB-6376 (lane c). Experiment 4. HeLa-tat$_{III}$ cells transfected with plasmids, pIIIAR (lane a); pAR-1SV (lane b); and pAR-1SVR (lane c).

In the absence of art, the level of CAT activity observed in cells transfected with plasmids pAR-2 and pAR-6 was similar to the activity obtained with the parental pIIIAR plasmid. All three of these plasmids direct similar levels of CAT activity and show substantial increases in the level of CAT enzyme activity upon co-transfection with plasmid pH3-art (16 to 24 fold increases in HeLa-tat$_{III}$ cells and 17 to 39 fold increases in the Jurkat-tat$_{III}$ cell line). The deletion present on plasmid pAR-6 removes the splice acceptor site for the env gene intron as well as the 3' coding exons for both the tat and art genes. Removal of these regions affects neither the CRS nor the CAR sequences. The experiments demonstrate that neither the splice acceptor nor splice donor sites that lie within the env gene are required for the inhibitory regulatory or art responsive anti-inhibitory effects.

Comparison of the level of CAT enzyme activity obtained in the absence of art in cells transfected with plasmids pAR-3 and pAR-7 to that observed upon transfection with plasmid pIIIAR reveals that the level of CAT activity is increased by about 10 fold by both of these deletions. However, the level of CAT activity can be increased further by co-transfection with plasmid pH3-art, an increase of about 2.5 fold in the HeLa-tat$_{III}$ cells and about 5 to 9 fold in the Jurkat-tat$_{III}$ cells. Evidently sequences that negatively regulate CAT gene expression are removed from these plasmids. However, these two deletions do not entirely eliminate the response to the art gene product. These experiments indicate that the proviral sequences present in plasmid pIIIAR contain at least two distinct sequences that can reduce the level of heterologous gene expression.

The level of CAT activity directed by plasmids pAR-4 and pAR-5 that contain large deletions in the central region of the intron removed from the tat and art mRNA was unaffected by the presence of the art gene product (Table 1). Evidently, these deletions remove all of the CAR sequences in the 3' half of the provirus. The CAR sequences therefore lie between nucleotides 6376 and 7683.

The level of CAT activity directed by plasmid pAR-4 in the absence of the art gene product was similar to that directed by pIIIAR (Table 1). However, the level of CAT enzyme activity was ten times greater in cells transfected with the pAR-5 plasmid than it was in cells transfected with either plasmid pAR-4 or pIIIAR. This result shows that CRSs present on plasmid pAR-4 that repress the activity of the CAT gene are removed by the larger deletions present in the pAR-6 plasmid.

Role of the 3'LTR Sequences for the Art Response

A set of plasmids were constructed in which the 3' HIV-I LTR sequences were replaced with the polyadenylation signals of SV40 virus as discussed above (FIG. 63). These plasmids also contain additional deletions of the proviral env gene sequences. In the absence of the art gene product, the level of CAT enzyme activity directed by plasmids pAR-1SV or pAR-2SV was similar to that directed by the parental pIIIAR plasmid in all recipient cell lines (Table 1). The level of CAT enzyme activity directed by these plasmids was increased 20 to 40 fold in cells simultaneously transfected with plasmid pH3-art. In the absence of art, the CAT activity obtained in cells transfected with plasmid pA-3SV, in which an additional region of the provirus was removed, was greater than that observed with either plasmids PIIIAR, pAR-1SV or pAR-2SV. Nonetheless, the level of CAT activity directed by this plasmid was increased about 7 fold in the presence of art. These results demonstrate that the 3'LTR is not required for art regulation and that the sequences remaining in the pAR-3SV plasmid retain a CAR element. The art-responsive CAR element in pAR-3SV appears to be located in sequences present between nucleotides 6583 and 7163 as plasmid pAR-4 that contains the same 3' proviral sequences from nucleotide 7683 to nucleotide 8561 is not art responsive.

Precise Mapping of a CAR Sequence

A set of nested deletions were made starting with plasmid pA-6376 that contains nucleotides 6376 to 7760 (FIG. 8), a region of the provirus that includes both the CRS and CAR sequences (Table 1). An SV40 polyadenylation sequence is located 3' to the proviral sequences in this plasmid. The level of CAT enzyme activity directed by plasmid pA-6376 in the absence of the art gene was similar to that observed for the pAR-SV1 plasmid that contains an extensive deletion of the 5' and 3' proviral sequences (Table 1). The level of CAT enzyme activity directed by plasmids pARoSV1 and pA-6376 was increased substantially upon co-transfection with the PH3-art plasmid.

Deletion of about 350 additional nucleotides from the 5' end of the proviral sequences on plasmid pA-6376 to yield plasmid pA-6725 (FIG. 8) resulted in an increase of about 10 to 20 fold in the level of CAT activity relative to pA-6376 in the absence of the art product (Table 1). The level of CAT gene expression was further increased 5 to 6 fold in the presence of art. Deletion of a similar region of proviral sequences from a different plasmid (compare PIIIAR to pAR-3SV, Table 1) also led to an increased level of CAT enzyme activity relative to the activity of plasmid PIIIAR (Table 1) also led to an increased level of CAT enzyme activity relative of the activity of plasmid PIIIAR (Table 1). These observations point to the existence of a CRS located between nucleotides 6583 and 6725, sequences that lie entirely within the coding region of the env gene.

Sequential deletion of additional nucleotides to yield plasmids pA-7000 to pA-7283 (FIG. 8) did not significantly alter the level of CAT enzyme activity observed in cells transfected in the absence of art as compared to the enzyme activity directed by the pA-6725 plasmid (Table 1). The level of gene expression observed in cells transfected with these plasmids was substantially increased by co-transfection with plasmid pH3-art. The art response is retained even though one of the regions that contain a CAR element, nucleotides 6583 and 7163 in plasmid pAR-3SV, is entirely deleted in plasmids pA-7201 and pA-7283.

Figure 2B:
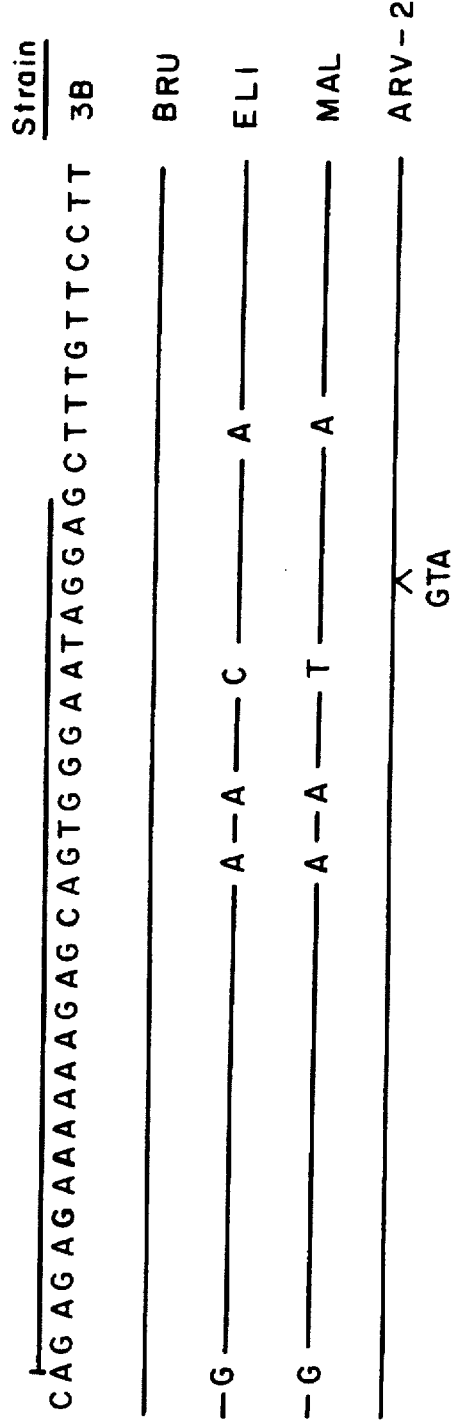
FIG. 2B shows nucleotide sequences required for $CAR_2$ activity.

Deletion of an additional 42 nucleotides from pA-7283 to yield pA-7325 results in a plasmid that does not show an increased level of gene expression in the presence of art. The level of CAT enzyme activity directed by plasmid pA-7325 was slightly higher than that directed by plasmids pA-6725 to pA-7283 in the absence of art. Plasmids that contain even larger deletions, pA-7441, pA-7510 and pA-7545 demonstrated levels of activity similar to that of plasmid pA-7325. Moreover, no increase in CAT enzyme activity directed by these plasmids was detected upon co-transfection with plasmid pH3-art. In these experiments, the minimum segment that contains CAR sequences responsive to the art gene is a 400 nucleotide proviral fragment located between nucleotides 7283 and 7760. An additional plasmid pB-6376, that contains proviral sequences extending from nucleotides 6376 and 6970 followed by the SV40 polyadenylation signal was constructed. The data of Table 1 and FIG. 7 show that the level of CAT enzyme activity directed by this plasmid in HeLa-tat$_{III}$ and CHO-tat$_{III}$ was unaffected by co-transfection with plasmid pH3-art. The low basal activity relative to pU3R-III suggests the existence of a CRS within the region 6376 to 6970. The lack of art-responsiveness suggests that the art-responsive CAR element located within nucleotides 6583 to 7163 is disrupted in plasmid pB-6376. The sequences necessary for CAR$_2$ function mapped in plasmid HXBc2 (Strain 3B) is shown in FIG. 2B. The purine-rich stretch is overlined. The CAR$_2$ sequence identified in Strain 3B [Ratner et al, *Nature* 313:277–284 (1985)] was aligned to the respective region present in strains, BRU [Wain-Hobson et al, *Cell* 40:9–17 (1985)], MAL (M. Alizon, personal communication), ELI (M. Alizon, personal communication), and ARV-2 [Sanchez-Pescador et al., *Science* 277:484–492 (1985)].

Orientation Dependence of the Art Response

As described above, the level of CAT enzyme activity directed by plasmid pAR-1SV was significantly increased (16 to 43 fold) in the presence of the art gene product. The effect of orientation of the CAR sequences with respect to the promoter and polyadenylation sequences was shown using a plasmid (pAR-1SVR) that contains the proviral sequences identical to those present in the pAR-1SV plasmid but in an inverse orientation (FIG. 6B). The level of CAT enzyme activity directed by plasmid pAR-1SVR was similar to that directed by plasmid pAR-1SV in the absence of art. No increase in the level of CAT enzyme activity was observed upon co-transfection of plasmid pAR-1SVR with pH3-art. The reduced level of activity relative to plasmid pU3RoIII indicates that the function of the CRS within this construct is orientation independent.

Absence of Enhancer Activity within the Env Gene Sequences

With the exception of enhancer elements, the location of the CAR sequences within the coding region distinguish this element from previously identified cis-acting regulatory sequences. To determine whether sequences within the env gene could regulate CAT gene expression when located 5' to the site of transcriptional initiation, plasmids were constructed in which portions of the env gene were placed 5' to a promoter that lacks an enhancer sequence (FIG. 9). The promoter used for these experiments was derived from the HTLV-I LTR and contains sequences −55 to +325 that have been shown previously to be responsive to heterologous enhancer sequences. The level of CAT enzyme activity directed by the plasmids that contain the env gene sequences located 5' to the promoter (pC-55/III 1470 and pC-55/III 2479) was similar to the activity observed with plasmid pC-55 that contains the HTLV-I promoter alone (Table 3). No increase in CAT activity was noted for these plasmids upon co-transfection with plasmid pH3-art. This indicates that the HIV-I sequences used in these experiments have no enhancer activity in the presence or absence of the art product.

TABLE 3

Activity of HIV env gene sequences in an enhancer assay.

| Experiment | pH3-art[b] | Relative CAT Activity[a] Cell Line | | | | | |
|---|---|---|---|---|---|---|---|
| | | HeLa-tat-III | | | CHO-tat-III | | |
| | | − | + | ( )[c] | − | + | ( )[c] |
| 1 | pC-55 | 1.00 | 0.82 | (0.8) | | | |
| | pC-55/III2479 | 1.00 | 0.88 | (0.9) | | | |
| | pC-55/III1470 | 0.71 | 0.79 | (1.6) | | | |
| 2 | pU3R-III | 1.00 | 1.30 | (1.3) | 1.00 | 1.40 | (1.4) |
| | pAR-1SV | 0.02 | 0.62 | (31) | 0.06 | 0.82 | (14) |
| | pAR-1SVR | 0.05 | 0.05 | (1.0) | 0.12 | 0.10 | (0.8) |

[a]Cells were transfected with 3 µg of the indicated plasmid DNA plus 3 µg of either non-specific competitor plasmid pU3R-IIIB or plasmid pH3-art. CAT assays were performed 48 hours after transfection. The absolute CAT activity was normalized to the value obtained following transfection plasmid pC-55 (Experiment 1) or pU3R-III (Experiment 2) in the absence of art.
[b]The induction value shown in parentheses were obtained by dividing the relative CAT activity obtained in the absence of art by the relative CAT activity obtained in the presence of art.

CAR Sequences in the Gag and Env Leader Sequences

Plasmids were constructed that contain portions of the 5' end of these genes inserted between the HIV-I LTR and the CAT gene (FIG. 10A and 10B). Transfection of HeLa-tat$_{III}$ and CHO-tat$_{III}$ cells with plasmids pLenv-314 and pLenv-100 as well as plasmids pLgag-321 resulted in high levels of CAT enzyme activity.

Schematic representation and activity of hybrid plasmids that contain the gag and env gene leader region sequences are shown in FIG. 10. The indicated portion of either env gene (FIG. 10A) or gag gene (FIG. 10B) leader sequence was cloned 3' to HIV-I sequences (nucleotide −167 to +80) and 5' to the CAT gene. The number used in the name of each plasmid is indicative of the number of HIV-I base pairs present in each hybrid construct. CAT activity of each plasmid was normalized to that obtained with plasmid pU3R-III (+++). The frame signifies whether the HIV-I sequences are in the same (IN) or different (OUT) translation reading frame of the CAT gene. Intitation codon (o) and stop codon (□) are shown.

The level of CAT enzyme activity was not increased upon co-transfection of these plasmids with plasmid pH3-art. No CAT activity was detected in cells transfected with plasmids pLenv-317 or pLgag-404. The reading frame of the gag and env gene of these two plasmids is the same as that for the CAT gene. The reading frame of the env gene AUG in plasmids pLenv-314 and pLenv-100 and that of the gag gene AUG in plasmid pLgag-321 is different from that of the CAT gene. Thus, it is likely that the inability of the pLenv-317 and pLgag-404 plasmids to direct CAT gene expression is due to interference with the initiation of protein synthesis of the CAT gene by the inframe initiation codon located 5'. These results are consistent with other reports which indicate that an upstream AUG codon will interfere with downstream initiation most effectively when the translation reading frame is identical to that of the downstream gene.

It is evident that those skilled in the art, given the benefit of the foregoing disclosure, may make numerous other uses and modifications thereof and departures from the specific embodiments described herein without departing from the inventive concepts, and the present invention is to be limited solely by the scope and spirit of the appended claims.

We claim:

1. A nucleotide region which contains both cis-acting repression sequences (CRS) and a cis-acting anti-repression sequence (RRE), said region consisting of the intron located between a major splice donor site in the env gene and a major splice acceptor site in the env gene, said env gene selected from the group consisting of HIV-I, HIV-2, HTLV-IV, STLV-3, and a sufficient fragment of said nucleotide region to suppress expression of a heterologous gene when said region is inserted downstream of said heterologous gene in said gene's untranslated message.

2. The nucleotide region of claim 1, wherein the cis-acting anti-repression sequence (RRE) present is sufficient to counteract the cis-acting repression sequences (CRS), and wherein said counteraction occurs in the presence of an effective amount of the rev (art) gene product.

3. A cis-acting repression sequence (CRS) selected from the group consisting of HIV-I nucleotides 6376–6725, 7283–7325, 5893–6538, 8204–8597, and a sufficient fragment thereof to suppress the expression of a heterologous gene, when said CRS is inserted downstream of said heterologous gene in said gene's untranslated message.

4. The cis-acting repression sequence (CRS) of claim 3, which consists of nucleotides 6376–6725 of HIV-I.

5. The cis-acting repression sequence (CRS) of claim 3, which consists of nucleotides 7283–7325 of HIV-I.

6. The cis-acting repression sequence (CRS) of claim 3, which consists of nucleotides 5893–6538 of HIV-I.

7. The cis-acting repression sequence (CRS) of claim 3, which consists of nucleotides 8204–8597 of HIV-I.

8. A cis-acting anti-repression sequence (RRE) which consists of HIV-I nucleotides 7283–7760.

9. The cis-acting anti-repression sequence (RRE) of claim 8, or a sufficient fragment thereof which counteracts the cis-acting repression sequence (CRS) inserted downstream of said heterologous gene in said gene's untranslated message, wherein said CRS is selected from the group consisting of HIV-I nucleotides 6376–6725, 7283–7325, 5893–6538, 8204–8597, and a sufficient fragment thereof to suppress the expression of said heterologous gene, and wherein said counteraction occurs in the presence of an effective amount of the rev (art) gene product.

10. A cis-acting anti-repression sequence (RRE) which comprises a sufficient fragment of a region consisting of the intron located between a major splice donor site and a major splice acceptor site in the env gene, said env gene selected from the group consisting of HIV-I, HIV-2, HTLV-IV and STLV-3, to counteract the cis-acting repression sequence (CRS) inserted downstream of a heterologous gene in said gene's untranslated message, wherein said CRS is selected from the group consisting of HIV-I nucleotides 6376–6725, 7283–7325, 5893–6538, 8204–8597, and a sufficient fragment thereof to suppress the expression of said heterologous gene, and wherein said counteraction occurs in the presence of an effective amount of rev (art) gene product.

11. A vector containing:
 (a) a gene which is heterologous to an HIV-I, HIV-2, HTLV-IV or STLV-3 genome, wherein downstream, in said heterologous gene's untranslated message, is inserted
 (b) a nucleotide region consisting of cis-acting repression sequence (CRS) and a cis-acting anti-repression sequence (RRE), said nucleotide region found within the intron located between a major splice donor site in the env gene and a major splice acceptor site in the env gene, said env gene selected from the group consisting of HIV-I, HIV-2, HTLV-IV, STLV-3, and a sufficient fragment thereof to suppress expression of said heterologous gene, and wherein the RRE present in the nucleotide region is sufficient to counteract this cis-acting repression effect on repression of the heterologous gene caused by the CRS, said counteraction occurring in the presence of an effective amount of the rev (art) gene product, and
 (c) a promotor operatively-lined 5' to the heterologous gene.

12. The vector of claim 11, wherein the CRS and the RRE are from HIV-I.

13. The vector of claim 11, wherein the CRS and RRE are from HIV-2.

14. The vector of claim 11, wherein the CRS and the RRE are from HTLV-IV.

15. The vector of claim 11, wherein the CRS and the RRE are from STLV-3.

16. The vector of claim 12 in which the promoter is an HIV-I LTR, and the vector further contains:
 (d) an HIV-I LTR 3' to the CRS and RRE.

17. The vector of claim 13 in which the promoter is an HIV-2 LTR, and the vector further contains:
 (d) an HIV-2 LTR 3' to the CRS and RRE.

18. The vector of claim 14 in which the promoter is an HTLV-IV LTR, and the vector further contains:
 (d) an HTLV-IV LTR 3' to the CRS and RRE.

19. The vector of claim 15 in which the promoter is an STLV-3 LTR, and the vector further contains:
 (d) an STLV-3 LTR 3' to the CRS and RRE.

20. A vector containing:
 (a) a gene which is heterologous to an HIV-I genome, wherein downstream, in said heterologous gene's untranslated message, is inserted
 (b) a nucleotide region consisting of nucleotides 6376–7760 of the HIV-I genome, said region containing both cis-acting repression sequences (CRS) and a cis-acting anti-repression sequence (RRE), and
 (c) a promoter operatively-linked 5' to the heterologous gene.

21. A method for expressing a heterologous gene product which comprises:
 (a) transfecting a pre-selected cell line with the vector of claim 11, and
 (b) contacting the RRE with an effective amount of the rev (art) gene product to activate the RRE and counteract the cis-acting repression effect on expression of the heterologous gene caused by the CRS, thereby expressing the heterologous gene product.

22. The method of claim 21, wherein the pre-selected cell line is a tat cell line containing a tat gene obtained from a viral species selected from the group consisting of HIV-I, HIV-2, HTLV-IV and STLV-3, and wherein the promoter operatively-linked 5' to the heterologous gene is an LTR from the same viral species as that from which the tat gene was obtained.

23. The method of claim 22, wherein the RRE is contacted with the rev (art) gene product in said cell line.

24. The method of claim 23, wherein said second vector expresses the rev (art) gene product under the control of a regulatable promoter which can be activated to express an effective amount of the rev (art) gene product to activate the RRE.

25. A method for expressing a heterologous gene product which comprises:
 (a) transfecting a pre-selected cell line with the vector of claim 20, and
 (b) contacting the RRE with an effective amount of the rev (art) gene product to activate the RRE and counteract the cis-acting repression effect on expression of the heterologous gene caused by the CRS thereby expressing the heterologous gene product.

26. The method of claim 25, wherein the promoter is the HIV-I LTR.

27. The method of claim 26, wherein the pre-selected cell line is a $tat_{III}$ cell line.

* * * * *